United States Patent [19]
Bourrain et al.

[11] Patent Number: 5,696,110
[45] Date of Patent: *Dec. 9, 1997

[54] BENZODIAZEPINE DERIVATIVES AND THEIR USE AS ANTAGONISTS OF CHOLECYSTOKININ AND/OR GASTRIN RECEPTORS

[75] Inventors: Sylvie Bourrain, Harlow; Stephen Robert Fletcher, Hatfield Heath; Victor Giulio Matassa, Furneux Pelham; Graham Andrew Showell, Welwyn Garden City, all of United Kingdom

[73] Assignee: Merck, Sharp & Dohme, Ltd., Hoddesdon, England

[*] Notice: The term of this patent shall not extend beyond the expiration date of Pat. No. 5,618,812.

[21] Appl. No.: 523,661

[22] Filed: Sep. 5, 1995

Related U.S. Application Data

[63] Continuation of Ser. No. 211,870, filed as PCT/GB92/01936, Oct. 21, 1992, abandoned.

[30] Foreign Application Priority Data

| Oct. 24, 1991 | [GB] | United Kingdom | 9122634 |
| Feb. 13, 1992 | [GB] | United Kingdom | 9203085 |
| Apr. 13, 1992 | [GB] | United Kingdom | 9208107 |
| Jul. 8, 1992 | [GB] | United Kingdom | 9214544 |

[51] Int. Cl.$^6$ .............. A61K 31/55; C07D 401/04; C07D 403/04; C07D 413/04
[52] U.S. Cl. .............. 514/211; 514/212; 514/221; 540/467; 540/480; 540/509
[58] Field of Search .............. 514/221, 211, 514/212; 540/509, 467, 480

[56] References Cited

U.S. PATENT DOCUMENTS

| 5,302,591 | 4/1994 | Fletcher et al. | 514/221 |
| 5,360,802 | 11/1994 | Chambers et al. | 514/221 |
| 5,410,049 | 4/1995 | Chambers | 540/504 |
| 5,451,582 | 9/1995 | Chambers et al. | 514/221 |
| 5,478,933 | 12/1995 | Showell | 540/509 |

FOREIGN PATENT DOCUMENTS

| 0 434 364 A3 | 12/1990 | European Pat. Off. |
| 0 434 369 A1 | 12/1990 | European Pat. Off. |

OTHER PUBLICATIONS

"Biological Properties of the Benzodiazepine Amidine Derivative L-740,093 . . . " by S. Patel et al., Am. Soc. Pharm. Exp. Ther., 46: pp. 943–948, 1994.

"The Effect of Cholecystokinin Receptor Antagonists MK-329 and L-365,260 . . . " by S. Kawabata et al., Regulatory Peptides, vol. 35 (1991), pp. 1–10.

SOCMA Handbook, Amer. Chem. Soc., 1965, p. 554.

M. G. Bock, et al. J. Med. Chem., 1989, 32, 16–23, "Benzodiazepine Gastrin and Brain CCK Receptor Ligands L-365,260".

G. N. Woodruff et al., Neuropeptides, vol. 19, Suppl., pp.45–46 (1991), "Functional Role of Brain CCK Receptors".

A. Hassner et al., Chem. Comm. pp. 590–591 (1967) "A New Synthesis of Amines with Diborane".

Westenberg, et al., New Chemical Drug Eval. Unit, 34th Annual Meeting (31 May 1994), Univ. of Utrecht, Session B "Effects of CCK-B Antagonist L-365,260 on Lactate Induced Panic . . .".

J. M. Gorman et al., Handbook of Anxiety, vol. 3, Neurobiology of Anxiety (1990) "Biological Models of Panic Disorder".

Merck Index, Eighth Edition, p. 941, (1968).

M. F. O'Neill et al., Brain Research, vol. 534, pp. 287–290 (1990) "Blockade of CCK-B receptors by L-365,260 . . . ".

Primary Examiner—Mark L. Berch
Attorney, Agent, or Firm—Robert J. North; Melvin Winokur

[57] ABSTRACT

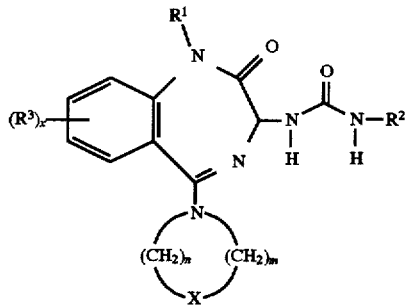

Compounds of formula (I), and salts and prodrugs thereof, wherein X is $O, S, NR^4$ or $CH_2$; $R^1$ represents H, certain optionally substituted $C_{1-6}$alkyl, or $C_{3-7}$cycloalkyl; $R^2$ represents phenyl having certain optional substituents; $R^3$ represents $C_{1-6}$alkyl, halo or $NR^6R^7$; m is 2,3 or 4; n is 1,2,3,4,5,6 7 or 8 when X is $CH_2$ or 2,3,4,5,6,7 or 8 when X is O, S or $NR^4$; and x is 0,1,2, or 3; are CCK and/or gastrin antagonists. They and compositions thereof are therefore useful in therapy.

11 Claims, No Drawings

BENZODIAZEPINE DERIVATIVES AND THEIR USE AS ANTAGONISTS OF CHOLECYSTOKININ AND/OR GASTRIN RECEPTORS

This is a continuation of application Ser. No. 08/211,870 filed Apr. 20, 1994, ABN which is a 371 of PCT/GB92/01936 filed Oct. 21, 1992.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, Biochem. J. 125, 678 (1971)), its carboxy-lterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin recaptots: implications for behavioral actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolongling opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin. CCK may function as a mediator of responses to stress and as part of the arousal system. CCK-A receptors are now known to be present in a number of areas of the CNS and may be involved in modulating any of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain rumours [K. Okyama, *Hokkaido J. Med. Sci.*, 206–216 (1985)], antagonists of CCK and gastrin are useful in treating these rumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (*Eur. J. Pharmacol.*, 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 167 919 discloses benzodiazepine CCK and gastrin antagonists substituted in the 3-position by, inter alia, a phenyl urea and at the 5-position by an optionally substituted phenyl or pyridyl group.

U.S. Pat. No. 3,414,563 discloses benzodiazepine derivatives optionally substituted at the 3-position by $C_{1-4}$alkyl or phenyl and substituted at the 5-position by a 3 to 8-membered azacycle, bound through nitrogen, which azacycle may optionally contain a further O, S or N atom. The compounds are said to have CNS activity. There is no suggestion of 8 nitrogen-containing substituent at the 3-position. Nor is there any suggestion that the disclosed compounds are antagonists at CCK or gastrin receptors.

The present invention provides benzodiazepine compounds of formula (I):

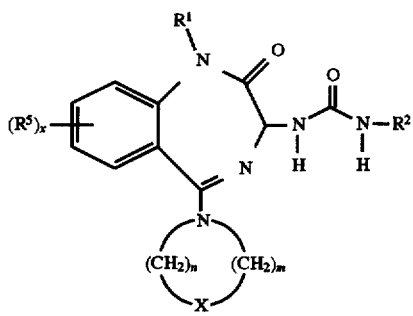

wherein:

X represents O, S, $NR^4$ or $CH_2$ where $R^4$ represents H, $C_{1-4}$alkyl, $CO_2R^a$, $COR^a$ or $SO_2R^a$ where $R^a$ is $C_{1-6}$alkyl, optionally substituted phenyl or benzyl optionally substituted in the phenyl ring by one or more substituents, where the phenyl substituents are selected from $C_{1-4}$alkyl, $C_{1-4}$alkoxy, halo and trifluoromethyl;

$R^1$ represents H, $C_{1-6}$alkyl, $C_{3-7}$cycloalkyl, cyclopropylmethyl, $(CH_2)_r$imidazolyl, $(CH_2)_r$triazolyl, $(CH_2)_r$tetrazolyl (where r is 1, 2 or 3), $CH_2CO_2R^5$ (where $R^5$ is $C_{1-4}$alkyl) or a group $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);

$R^2$ represents a phenyl group optionally substituted by one or more substituents selected from $C_{1-6}$alkyl, halo, hydroxy, $OR^5$ (where $R^5$ is as previously defined), $(CH_2)_q$-tetrazolyl optionally substituted in the tetrazole ring by $C_{1-4}$alkyl, $(CH_2)_q$-imidazolyl, $(CH_2)_q$-triazolyl (where q is 0, 1, 2 or 3), 5-hydroxy-4-pyrone, $NR^6R^7$, $NR^9COR^5$, $NR^9CONR^9R^5$ (where $R^9$ and $R^{9'}$ are each independently H or $C_{1-4}$alkyl and $R^5$ is as previously defined), $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl, 2,2-difluorocyclopropane or trifluoromethyl), $SO_2NHR^{10}$ (where $R^{10}$ is a nitrogen containing heterocycle), $B(OH)_2$, $(CH_2)_qCO_2H$, where q is as previously defined; or $R^2$ represents a group

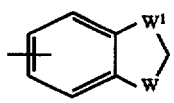

where W represents $CH_2$ or $NR^9$, where $R^9$ is as previously defined, and $W^1$ represents $CH_2$, or W and $W^1$ each represent O;

$R^3$ represents $C_{1-6}$alkyl, halo or $NR^6R^7$, where $R^6$ and $R^7$ are as previously defined;

m is 2, 3 or 4;

n is 1, 2, 3, 4, 5, 6, 7 or 8 when X is $CH_2$, or 2, 3, 4, 5, 6, 7 or 8 when X is O, S or $NR^4$;

x is 0, 1, 2 or 3;

and salts and prodrugs thereof.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, unless otherwise indicated, alkyl means saturated hydrocarbon having straight or branched groups, or combinations thereof.

Unless otherwise stated, aryl means optionally substituted carbocyclic or heterocyclic aromatic groups, especially phenyl.

Heteroaryl means aromatic rings preferably having 5 or 6 ring atoms and containing at least one atom selected from O, S and a group $NR^5$, where $R^5$ is as previously defined.

When $R^1$ is $C_{3-7}$cycloalkyl, suitable cycloalkyl groups include cyclopropyl, cyclopentyl and cyclohexyl groups, preferably cyclopropyl.

When $R^8$ is optionally substituted aryl, this will preferably be optionally substituted phenyl. Suitable substituents include $C_{1-4}$alkyl, $C_{1-4}$alkoxy, halo and trifluoromethyl. Preferred is unsubstituted phenyl or phenyl substituted by $C_{1-6}$alkyl, for example, phenyl substituted by $C_{1-6}$alkyl, such as methyl, in the ortho position.

When $R^8$ is $C_{1-6}$alkyl, it will preferably represent $C_{1-4}$alkyl. Particularly preferred are methyl and iso-propyl, especially iso-propyl.

Halo includes fluoro, chloro and bromo. In compounds of formula (I), halo will preferably be fluoro or chloro.

In a subgroup of compounds of formula (I), $R^1$ represents $C_{1-6}$alkyl, $C_{3-7}$cycloalkyl, cyclopropylmethyl, $CH_2CO_2R^5$ (where $R^5$ is $C_{1-4}$alkyl) or a group $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5); and $R^2$ represents a phenyl group optionally substituted by one or more substituents selected from $C_{1-6}$alkyl, halo, hydroxy, $OR^5$ (where $R^5$ is as previously defined), $(CH_2)_q$-tetrazolyl optionally substituted in the tetrazole ring by $C_{1-4}$alkyl, $(CH_2)_q$-imidazolyl, $(CH_2)_q$-triazolyl (where q is 1, 2 or 3), 5-hydroxy-4-pyrone, $NR^6R^7$, $NR^9COR^5$, $NR^9COR^9R^5$ (where $R^9$ and $R^{9'}$ are each independently H or $C_{1-4}$alkyl) $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl, 2,2-difluorocyclopropane or trifluoromethyl), $SO_2NHR^{10}$ (where $R^{10}$ is a nitrogen containing heterocycle), $B(OH)_2$, $(CH_2)_sCO_2H$, where s is zero, 1 or 2; or $R^2$ represents a group

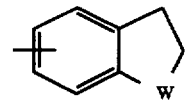

where W represents $CH_2$ or $NR^9$, and $R^9$ is as previously defined, and m is 2.

A further subgroup of compounds according to formula (I) is represented by formula (Ia):

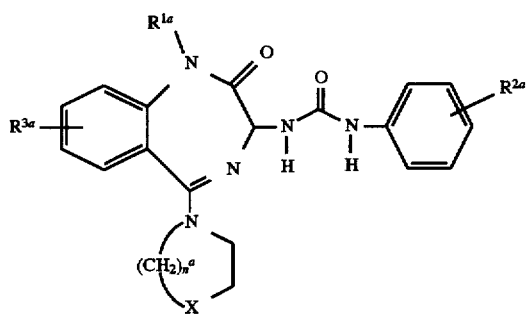

wherein:

X is as defined for formula (I);

R$^{1a}$ represents C$_{1-6}$alkyl, C$_{3-7}$cycloalkyl, cyclopropylmethyl, CH$_2$CO$_2$R$^5$ (where R$^5$ is C$_{1-4}$alkyl) or a group CH$_2$CONR$^6$R$^7$ (where R$^6$ and R$^7$ each independently represents H or C$_{1-4}$alkyl, or R$^6$ and R$^7$ together form a chain (CH$_2$)$_p$ where p is 4 or 5);

R$^{2a}$ represents H, C$_{1-6}$alkyl, halo, hydroxy, OR$^5$ (where R$^5$ is as previously defined), (CH$_2$)$_{q^a}$-tetrazole optionally substituted on N by C$_{1-4}$alkyl, (CH$_2$)$_{q^a}$-imidazolyl, CONR$^6$R$^7$ (where R$^6$ and R$^7$ are as previously defined), trifluoromethyl, CONHSO$_2$R$^8$, SO$_2$NHCOR$^8$ (where R$^8$ is C$_{1-4}$alkyl, optionally substituted aryl or trifluoromethyl), SO$_2$NHR$^{10}$ (where R$^{10}$ is a nitrogen containing heterocycle), cyclopropyl or a group (CH$_2$)$_{q^a}$CO$_2$H, where q$^a$ is zero, 1 or 2;

R$^{3a}$ represents H, C$_{1-6}$alkyl or halo;

n$^a$ is 1, 2 or 3 when X is CH$_2$, or 2 or 3 when X is O, S or NR$^4$;

and pharmaceutically acceptable salts or prodrugs thereof.

A subgroup of compounds of formula (Ia) is represented by compounds wherein R$^2$ represents H, C$_{1-6}$alkyl, halo, (CH$_2$)$_q$-tetrazolyl, (CH$_2$)$_q$-imidazolyl, CONHSO$_2$R$^8$, SO$_2$NHCOR$^8$ (where R$^8$ is C$_{1-4}$alkyl, optionally substituted aryl or trifluoromethyl) or (CH$_2$)$_q$CO$_2$H, where q is zero, 1 or 2.

In the compounds of formula (I), X is preferably O, S, CH$_2$ or N(C$_{1-4}$alkyl), more preferably CH$_2$ or NCH$_3$, especially CH$_2$.

Preferably R$^1$ is C$_{1-6}$alkyl, more preferably C$_{1-4}$alkyl, such as methyl, ethyl, n-propyl or isobutyl.

Suitable values for R$^8$ include methyl, ethyl, i-propyl, t-butyl, phenyl, o-methylphenyl and trifluoromethyl.

When R$^2$ is phenyl substituted by SO$_2$NHR$^{10}$, suitable values of R$^{10}$ include, for example, thiazole, thiadiazole and pyrazine.

Preferably q is zero.

Preferably R$^2$ is phenyl substituted by methyl, ethyl, chloro, 5-hydroxy-4-pyrone, trifluoromethyl or dimethylamino; or R$^2$ is

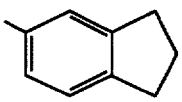

When R$^2$ represents monosubstituted phenyl, the substituent will preferably be located at the 3- or 4-position of the phenyl ring, more preferably the 3-position. When R$^2$ represents disubstituted phenyl, the substituents will preferably be located at the 3- and 4-positions. When R$^2$ represents a group

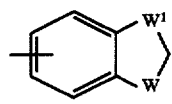

the fused 5-membered rang will preferably be fused across the 3 and 4 positions of the phenyl ring.

Suitable values for R$^3$ include methyl and dimethylamino.

Preferably x is 0 or 1, more preferably 0.

Preferably m is 2.

When X is O, S or NR$^4$, n is preferably 2 or 3. When X is CH$_2$, n is preferably 2, 3, 4 or 5, more preferably 3, 4 or 5, especially 3.

Suitable examples of the 5-substituent

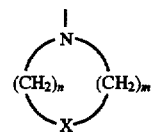

include:

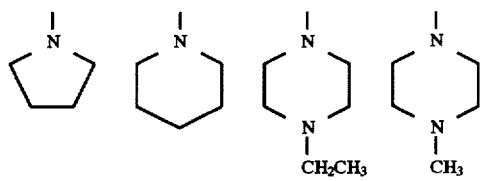

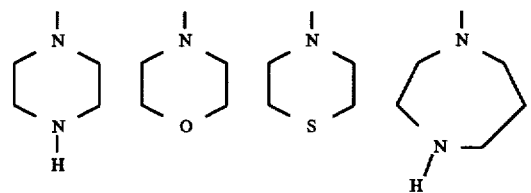

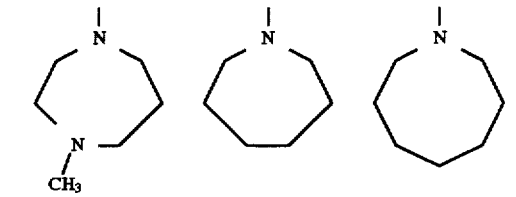

Preferred values of the 5-substituent are homopiperidine, N-methylpiperazine, heptamethyleneimine and octamethyleneimine, especially homopiperidine.

A preferred subgroup of compounds according to the invention is represented by formula (Ib)

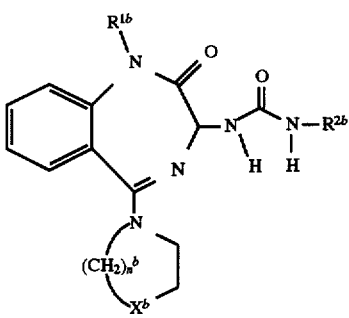

wherein:

$X^b$ represents O, S, $NR^{4b}$ or $CH_2$, where $R^{4b}$ represents H or $C_{1-4}$alkyl; preferably $C_{1-2}$alkyl;

$R^{1b}$ represents $C_{1-6}$alkyl, preferably $C_{1-4}$alkyl;

$R^{2b}$ represents a phenyl group optionally substituted by one or two substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, where q is 0, 1, 2 or 3, 5-hydroxy-4-pyrone, $NR^6R^7$ (where $R^6$ and $R^7$ are as previously defined), $NR^9COR^5$, $NR^9CONR^9R^5$ where $R^5$, $R^9$ and $R^{9'}$ are as previously defined, $CONR^6R^7$ or trifluoromethyl; or $R^{2b}$ represents a group

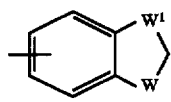

where W and $W^1$ are as previously defined;

n is 1, 2, 3, 4 or 5 when $X^b$ is $CH_2$, or 2, 3, 4 or 5 when $X^b$ is O, S or $NR^{4b}$;

and salts and prodrugs thereof.

Particularly preferred are compounds of formula (1b) wherein $R^{1b}$ is methyl, ethyl or n-propyl; $R^{2b}$ is phenyl substituted in the 3-position by methyl, ethyl or 5-hydroxy-4-pyrone, or $R^{2b}$ is

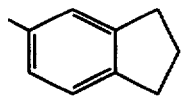

$X^b$ is $CH_2$ or $NCH_3$, more preferably $CH_2$; and n is 3, 4 or 5 where $X^b$ is $CH_2$ or 2 where X is $NCH_3$.

A particularly preferred compound according to formula (Ib) is (−)-N-[2,3-dihydro-5-(homopiperidin-1-yl)-1-methyl-2-oxo-1H-1,4-benzodiazepin-3-yl]-N -[3-methylphenyl]urea.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic salts. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic. Preferred salts of the compounds according to the invention are hydrohalide, especially hydrochloride, salts.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss, or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary rumours of the central nervous system glial and neuronal cells. Examples of such adenocarcinomas and rumours include, but are not limited to, rumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a rumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by reacting intermediates of formula (II) with compounds of formula (III)

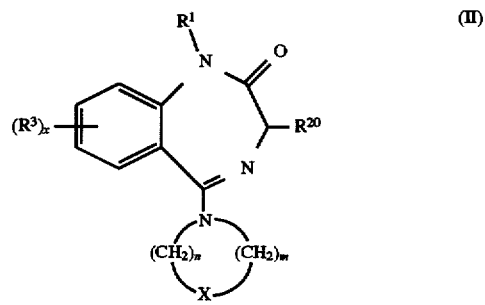

$$R^{21}-R^2 \quad \text{(III)}$$

wherein $R^1$, $R^2$, $R^3$, X, m, n and x are as defined for formula (I) above, and one of $R^{20}$ and $R^{21}$ represents $NH_2$ and the other of $R^{21}$ and $R^{20}$ represents —N=C=O.

The reaction is conveniently effected in a suitable organic solvent, such as an ether, for example, tetrahydrofuran.

Intermediates of formula (II) wherein $R^{20}$ represents $NH_2$ (IIA) may be prepared from compounds of formula (IV):

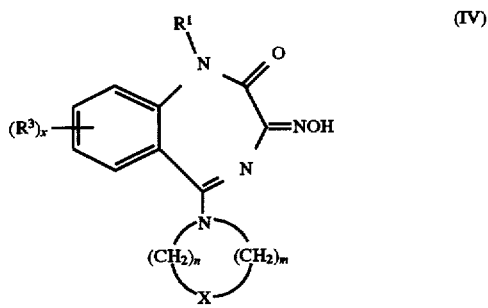

wherein $R^1$, $R^3$, X, m, n and x are as defined for formula (I) above, by reduction, for example, by catalytic hydrogenation or reduction using a suitable metal under acidic conditions.

Suitable hydrogenation catalysts include, for example, noble metal catalysts, e.g. ruthenium, or rhodium which may be supported, for example, on carbon.

The reaction is preferably conducted in a suitable organic solvent, such as an alcohol, for example, methanol, at elevated temperature, such as about 60° to 70° C., preferably about 60° C.

Suitable reduction methods using metals include, for example, the use of zinc and trifluoroacetic acid in a suitable solvent, such as acetic acid, preferably at elevated temperature, e.g. at about 40° C.

Preferably intermediates of formula (IIA) may be prepared from compounds of formula (V)

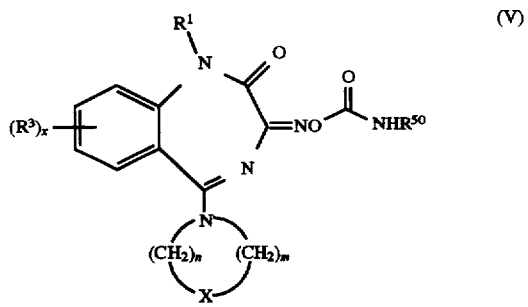

wherein $R^1$, $R^3$, X, m, n and x are as defined for formula (I) and $R^{50}$ represents alkyl, by reduction, for example, by catalytic hydrogenation.

Suitable hydrogenation catalysts include, for example, noble metal catalysts, such as palladium, which say be supported, for example, on carbon.

The reaction is conveniently conducted in a suitable organic solvent, such as an alcohol, for example, methanol, suitably at ambient temperature.

Intermediates of formula (II) wherein $R^{20}$ is —N=C=O (IIB) may be prepared from amines of formula (IIA) by reaction with triphosgene in the presence of a base, such as a tertiary amine, for example, triethylamine. The reaction is conveniently effected in a suitable organic solvent at low temperature, such as about 0° C.

Intermediates of formula (V) may be prepared from intermediates of formula (IV) by reaction with an isocyanate of formula $R^{50}N=C=O$, wherein $R^{50}$ is as previously defined.

The reaction is conveniently effected in a suitable organic solvent, such an ether, for example, tetrahydrofuran, suitably at elevated temperature, such as about 60° C.

Intermediates of formula (IV) may be prepared from compounds of formula (VI)

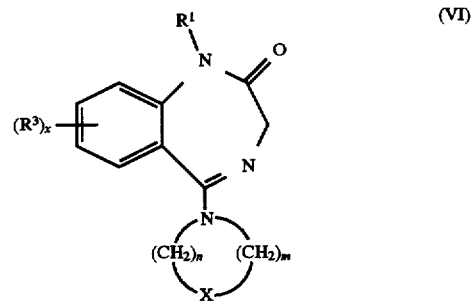

wherein $R^1$, $R^3$, X, m, n and x are as defined for formula (I), by reaction with isoamyl nitrite in the presence of a base.

Suitable bases of use in the reaction include alkali metal alkoxides, such as potassium t-butoxide.

Compounds of formula (VI) may be prepared from compounds of formula (VII)

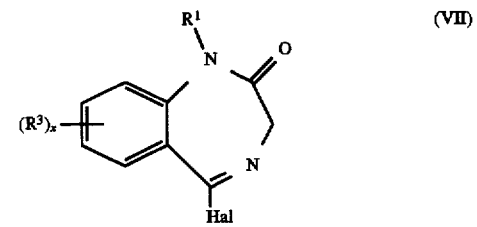

wherein $R^1$, $R^3$ and x are as defined for formula (I) and Hal represents halo, such as chloro, by reaction with a compound of formula (VIII)

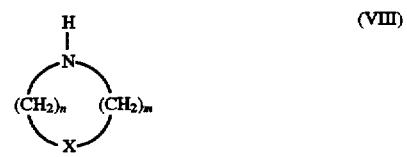

wherein X, m and n are as defined above.

The preparation of compounds of formula (VII) is described in United Kingdom Patent Specification No. 1,145,471.

Compounds of formula (VII) may be prepared from intermediates of formula (IX)

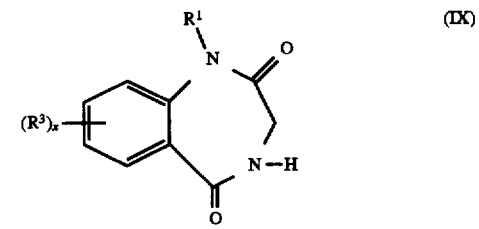

wherein $R^1$, $R^3$ and x are as defined for formula (I), by treatment with a halogenating agent, such as a phosphorus pentahalide, for example, phosphorus pentachloride.

The reaction is conveniently effected in a suitable organic solvent, such as a halogenated hydrocarbon, for example, dichloromethane.

Compounds of formula (IX) may be prepared from compounds of formula (X)

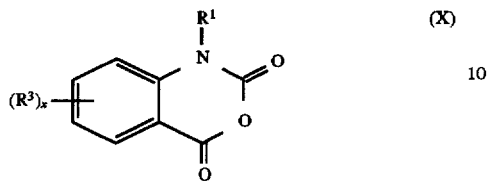

wherein $R^1$, $R^3$ and x are as previously defined, by treatment with glycine and acetic acid at elevated temperature.

Compounds of formula (X) may be prepared by the methods described in *J. Het. Chem.*, 1978, 15, 645–647, or methods analogous thereto.

Alternatively, compounds of formula (IX) may be prepared from compounds of formula (XI)

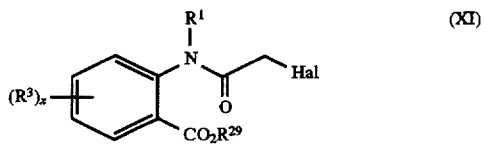

wherein $R^1$, $R^3$ and x are as previously defined, represents halo, such as bromo, and $R^{29}$ represents $C_{1-4}$alkyl, by treatment with ammonia.

The reaction is conveniently effected in a suitable organic solvent, such as an alcohol, e.g. methanol.

Compounds of formula (XI) may be prepared from compounds of formula (XII)

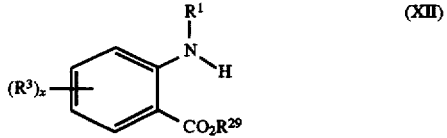

wherein $R^1$, $R^3$, $R^{29}$ and x are as previously defined, by treatment with a reagent of formula Hal-CH$_2$—CO-Hal, wherein Hal is as previously defined.

The reaction is conveniently effected in a suitable organic solvent, such as a halogenated hydrocarbon, e.g. dichloromethane.

Compounds of formula (XII) are known compounds or may be prepared from known compounds by conventional procedures. Suitable procedures are described in the accompanying examples. Alternative procedures will be readily apparent to those skilled in the art.

Intermediates of formulae (II), (III), (IV) and (V) are novel compounds and form a further aspect of the present invention.

The present invention therefore provides intermediates of formula (M)

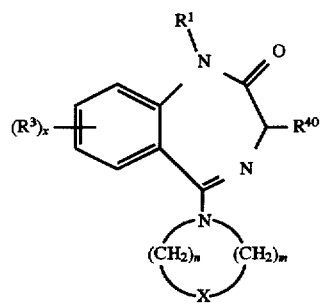

wherein $R^1$, $R^3$, X, m, n and x are as defined for formula (I) and $R^{40}$ represents $NH_2$, NOH, N=C=O or $NOCONHR^{50}$, where $R^{50}$ is as previously defined.

Where the above-described process preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R,S)-2,3-Dihydro-1-methyl-2-oxo-5-(piperidin-1-yl)-1H-1,4-benzodiazepin-3-yl]N'-[3-methylphenyl]urea.

Step A: Methyl 2-(N-bromoacetyl-N-methylamino) benzoate

Sodium hydroxide solution (1.5M, 50 ml) was added dropwise to an ice cooled mixture of bromoacetyl bromide (11 g) and methyl N-methylanthranilate (8.2 g) in dichloromethane (250 ml). After the addition was complete (15 min) stirring was continued at room temperature for 20 min. The organic phase was then separated, washed with 1N HCl (50 ml), brine (50 ml), NaHCO$_3$ solution (50 ml), dried (MgSO$_4$) and evaporated to give a colourless oil which crystallised on standing. Trituration with pet-ether (bp 60°–80°) followed by filtration afforded 10.4 g of product as a colourless solid. $^1$H NMR (360 MHz, CDCl$_3$) δ: 3.23 (3H, s), 3.54 and 3.60 (2H, ABq J=11 Hz), 3.90 (3H, s), 7.40 (1H, d, J=8 Hz), 7.51 (1H, t, J=8 Hz), 7.65 (1H, t, J=8 Hz), 8.04 (1H, d, J=8 Hz).

Step B: 1-Methyl-1,2,3,4-tetrahydro-3H-1,4 benzodiazepin-2,5-dione

Ammonia gas was bubbled through an ice-cooled solution of methyl 2-(N-bromoacetyl-N-methylamino)benzoate (10 g) in methanol (100 ml) for 2 h. The solvent was then evaporated and the residue partitioned between dichloromethane (150 ml) and citric acid (50 ml). The organic phase was separated, washed with brine (50 ml), dried (MgSO$_4$) and evaporated to give 5.7 g of product as a colourless solid, mp, 190°–3° C. $^1$H NMR (360 MHz, CDCl$_3$) δ: 3.42 (3H, s), 3.7–3.9 (2H, brs), 6.8 (1H, s), 7.24 (1H, d, J=8 Hz), 7.32 (1H, t, J=8 Hz), 7.57 (1H, t, J=8 Hz), 7.90 (1H, d, J=8Hz).

Step C: 5-Chloro-1,2-dihydro-1-methyl-3H-1,4-benzodiazepin-2-one hydrochloride

A solution of phosphorus pentachloride (1.2 g) in dichloromethane (50 ml) was added dropwise to a solution of 1-methyl-1,2,3,4-tetrahydro-3H-1,4-benzodiazepin-2,5-dione (0.9 g) in dichloromethane (20 ml) stirring at room temperature. After 2 h the solvent was evaporated and the volatiles chased with toluene to afford product as an orange foam which was not purified further.

Step D: 1,2-Dihydro-1-methyl-5-(piperidin-1-yl)-3H-1,4-benzodiazepin-2-one

Piperidine (1.34 g) was added to a solution of crude 5-chloro-1,2-dihydro-1-methyl-3H-1,4-benzodiazepin-2-one hydrochloride (0.005 mol) in dichloromethane (50 ml) cooled in ice. After warming to room temperature, sodium bicarbonate solution (20 ml) was added. The organic phase was separated, dried (Na$_2$SO$_4$) and evaporated to give an orange oil which was purified by column chromatography on silica with CH$_2$Cl$_2$→CH$_2$Cl$_2$:MeOH 95:5 as eluant to afford 0.62 g of product as an orange gum $^1$H NMR (250 MHz, CDCl$_3$) δ: 1.5–1.8 (6H, m), 3.15–3.4 (4H, m), 3.4 (3H, s), 3.5 and 4.25 (2H, ABq, J=11Hz), 7.15–7.6 (5H, m).

Step E: 1,2-Dihydro-1-methyl-3-oximido-5-(piperidin-1-yl)-3H-1,4-benzodiazepin-2-one Potassium t-butoxide (0.65 g) was added portionwise to a solution of 1,2 dihydro-1-methyl-5-(piperidin-1-yl)-3H-1,4-benzodiazepin-2-one (0.55 g) in dry toluene (50 ml) cooled below −10°, under nitrogen. After 15 min isoamyl nitrite (0.33 ml) was added to one portion and stirring continued for 25 min. Citric acid (1M, 20 ml) was then added and the mixture extracted with ethyl acetate (4×50 ml). The combined organic phase was washed with water, dried (Na$_2$SO$_4$) and evaporated to give a gummy solid which was triturated with diethyl ether to give 0.32 g of product as a yellow solid, tlc (silica, CH$_2$Cl$_2$:MeOH 9:1), R$_f$ 0.6. $^1$H NMR (360 MHz, DMSO-d$_6$) δ1.35–1.55 (2H, m), 1.55–1.7 (4H, m), 3.3 (3H, s), 3.4–3.55 (4H, m), 7.30 (1H, t, J=8 Hz), 7.43 (1H, d, J=8 Hz), 7.50 (1H, d, J=8 Hz), 7.58 (1H, t, J=8 Hz).

Step F: 3-Amino-1,2-dihydro-1-methyl-5-(piperidin-1-yl)-3H-1,4-benzodiazepin-2-one A suspension of 1,2-dihydro-1-methyl-3-oximido-5-(piperidin-1-yl)-3H-1,4-benzodiazepin-2-one (0.24 g) and 5% ruthenium-on-carbon (0.16 g) in methanol (50 ml) was hydrogenated at 55 psi H$_2$ at 700 for 24 h. The catalyst was then removed by filtration and the solvent evaporated. The residue was purified by column chromatography on silica with CH$_2$Cl$_2$: MeOH 98:2→9:1 as eluant to afford 0.05 g of product as a colourless oil, Tlc (silica, CH$_2$Cl$_2$: MeOH 9:1), R$_f$ 0.4.

Step G: N-[3(R,S)-2,3 Dihydro-1-methyl-2-oxo-5-piperidin-1-yl)-1H-1,4-benzodiazepin-3-yl]N'-(3-methylphenyl)urea m-Tolyl isocyanate (0.025 g) was added in one portion to a solution of 3-amino-1,2-dihydro-1-methyl-5-(piperidin-1-yl)-3H-1,4-benzodiazepin-2-one (0.03 g) in THF (1 ml) at room temperature. After 5 min a solid precipitated which as collected by centrifugation to afford 0.03 g of product as a colourless powder. mp 241°–5°. $^1$H NMR (360 MHz, DMSO-d$_6$) δ1.35–1.55 (2H, m), 1.55–1.7 (4H, m), 2.21 (3H, s), 3.1–3.3 (4H, m), 3.33 (3H, s), 4.94 (1H, d, J=8 Hz), 6.7 (1H, d, J=8 Hz), 7.01–7.70 (8H, m), 8.55 (1H, s).

EXAMPLE 2

N-[3(R,S)-2,3-Dihydro-1-methyl-2-oxo-5-(pyrrolidin-1-yl)-1H-1,4-benzodiazepin-3-yl]N'-[3-methylphenyl]urea.

Carrying out Steps 1 A–G whilst replacing piperidine in Step 1D with pyrrolidine afforded the titled compound as a colourless powder, mp, 246°–80°. $^1$H NMR (360 MHz, DMSO-d$_6$) δ: 1.7–1.8 (2H, m), 1.8–1.9 (1H, m), 3.0–3.15 (2H, m), 3.3–3.5 (2H, m), 6.69 (1H, d J=8 Hz), 4.94 (1H, d J=8 Hz), 6.9–7.7 (8H, m), 8.80 (1H, s).

EXAMPLE 3

N-[3(R,S)-2,3-Dihydro-1-methyl-5-(morpholin-4-yl)-2-oxo-1H-1,4-benzodiazepin-3-yl]N'-[3-methylphenyl]urea.

Carrying out Steps 1A–G whilst replacing piperidine in Step 1D with morpholine afforded the titled compound as a colourless powder, mp, 260°–3°. $^1$H NMR (360 MHz, DMSO-d$_6$) δ: 2.20 (3H, s), 3.05–3.2 (4H, m), 3.35 (3H, s), 3.6–3.70 (2H, m), 3.70–3.8 (2H, m), 4.98 (1H, d, J=8 Hz), 6.71 (1H, d J=8 Hz), 7.10–7.70 (8H, m), 8.85 (1H, s). Found; C, 64.73; H, 6.42; N, 16.83. C$_{22}$H$_{25}$N$_5$O$_3$ requires; C, 64.85; H, 6.18; N, 17.19.

EXAMPLE 4

N-[3(R,S)-2,3-Dihydro-1-methyl-5-(4-methylpiperazin-1-yl-2-oxo-1H-1,4-benzodiazepin-3-yl]N'-[3-methylphenyl]urea.

Carrying out Steps 1A–G whilst replacing piperidine in Step 1D with N-methylpiperazine afforded the titled compound as a colourless powder, mp, 220°–2° (EtOH). $^1$H NMR (260 MHz, CDCl$_3$) δ:2.4 (3H, s), 2.41 (3H, s), 2.41–2.7 (4H, m), 3.1–3.4 (4H, m), 3.5 (3H, s), 5.25 (1H, d, J=8 Hz), 6.45 (1H, d, J=8 Hz), 6.75 (1H, s), 6.8–7.6 (8H, m). Found: C, 64.92; H, 6.61; N, 19.63. C$_{23}$H$_{28}$N$_6$O$_2$.0.25H$_2$O requires C, 64.99; H, 6.76; N, 19.77%.

EXAMPLE 5

N-[3(R,S)-2,3-Dihydro-1-methyl-5-(4-methylpiperazin-1-yl)-2-oxo-1H-1,4-benzodiazepin-3-yl]N'-[3-ethylphenyl]urea.

Carrying out Steps 1A–G whilst replacing piperidine in Step 1D with N-methylpiperazine and m-tolyl isocyanate in Step 1G with 3-ethylphenyl isocyanate afforded the titled compound as a colourless powder, mp 218°–9° C. $^1$H NMR (360 MHz, CDCl$_3$) δ: 1.20 (3H, t, J=8 Hz), 2.31 (3H, s), 2.3–2.4 (2H, m), 2.45–2.6 (2H, m), 2.59 (1H, q, J=8 Hz), 3.2–3.4 (4H, m) 3.43 (2H, s), 5.28 (2H, d, J=8 Hz), 6.48 (2H, d, J=8 Hz), 6.78 (1H, s), 6.87 (1H, d, J=8 Hz), 7.08 (1H, d, J=8 Hz), 7.18 (1H, dd, J¹=8 J²=8 Hz), 7.22–7.28 (2H,m), 7.32 (1H, d J=8 Hz), 7.49–7.56 (2H, m). Found: C, 61.99; H, 7.04; N, 18.03. $C_{24}H_{31}N_6O_2 \cdot 1.75H_2O$ requires C, 61.85; H, 7.25; N, 18.03.

EXAMPLE 6

N-[3(R,S)-2,3-Dihydro-1-methyl-5-(4-methylpiperazin-1-yl)-2-oxo-1H-1,4-benzodiazepin-3-yl]N'-[4-methylphenyl]urea.

Carrying out Steps 1A–G whilst replacing piperidine in Step 1D with N-methylpiperazine and m-tolyl isocyanate in Step 1g with p-tolyl isocyanate afforded the titled compound as a colourless powder, mp, dec>240° (EtOH). ¹H NMR (360 MHz, CDCl₃) δ2.29 (3H, s), 2.31 (3H, s), 2.3–2.4 (2H, m), 2.4–2.5 (2H, m) 3.15–3.4 (4H, m), 3.42 (3H, s), 5.27 (1H, d, J=8 Hz), 6.48 (1H, d, J=8 Hz), 6.76 (1H, s), 7.08 (2H, d, J=8 Hz), 7.20–7.56 (6H, m).

EXAMPLE 7

N-[3(R,S)-2,3-Dihydro-1-methyl-5-(4-methylpiperazin-1-yl)-2-oxo-1H-1,4-benzodiazepin-3-yl]N'-[4-chlorophenyl]urea.

Carrying out Steps 1A–G whilst replaying piperidine in Step 1D with N-methylpiperazine and m-tolyl isocyanate in Step 1G with 4-chlorophenyl isocyanate afforded the titled compound as a colourless powder, mp, dec>200°. ¹H NMR (360 MHz, CDCl₃) δ2.35 (3H, s), 2.3–2.45 (2H, m), 2.5–2.6 (2H, m) 3.2–3.45 (4H, m), 3.42 (3H, s), 5.26 (1H, d, J=8 Hz), 6.65 (1H, d, J=8 Hz), 7.17–7.55 (9H, m).

EXAMPLE 8

N-[3(R,S)-2,3-Dihydro-5-(4-methylpiperazin-1-yl)-2-oxo-1-propyl-1H -1,4-benzodiazepin-3-yl]-N'-[3-methylphenyl]urea Step A: Methyl N-propyl anthranilate To a stirred solution of methyl anthranilate (10.0 g) in methanol (50 ml) was added propionitrile (4.77 ml) followed by glacial acetic acid (20 ml). Sodium cyanoborohydride (4.5 g) was added in portions over 30 minutes, maintaining the temperature below 30° C. After addition the reaction mixture was stirred for 2 hours. The solvents were evaporated in vacuo and the residue partitioned between ethyl acetate (50 ml) and 10% potassium carbonate solution (100 ml). The organic layer was separated and the aqueous re-extracted with ethyl acetate (2×50 ml). The combined organics were washed with brine, dried (sodium sulphate) then evaporated to give a yellow oil which was distilled under vacuum. The title product was obtained as a pale yellow oil (10.6 g), bp 138°–140° C. (0.3 mmHg). $R_f$ 0.65 in ethyl acetate/n-hexane (1:1) on silica plates. ¹H NMR (360 MHz, CDCl₃) δ1.03 (3H, t, J=7 Hz), 1.71 (2H, sextet, J=7 Hz), 5.15 (2H, q, J=7 Hz), 5.85 (3H, s), 6.56 (1H, dd, $J_1=J_2=8$ Hz), 6.67 (1H, d, J=8 Hz), 7.34 (1H, ddd, $J_1=J_2=8$ Hz, $J_3=3$ Hz), 7.69 (1H, broad resonance), 7.88 (1H, dd, $J_1=3$ Hz, $J_2=8$ Hz). Found: C, 66.79; H, 7.62; N, 7.33. $C_{11}H_{15}NO_2 \cdot 0.25H_2O$ requires C, 66.81; H, 7.90; N, 7.08%.

Step B: 1-Propyl-1,2,3,4-tetrahydro-3H-1,4-benzodiazepin-2,5-dione

Prepared from methyl-N-propyl anthranilate using the method described in Example 1. mp 137°–138° C. $R_f$ 0.20 in ethyl acetate/petroleum ether (60–80) (1:1) on silica plates. MS, CI⁺, m/z=219 for (M+H)⁺.

Step C: N-[3(R,S)-2,3-Dihydro-5-(4-methylpiperazin-1-yl)-2-oxo-1-propyl -1H-1,4-benzodiazepin-3-yl]-N'-[3-methylphenyl]urea Prepared from 1-propyl-1,2,3,4-tetrahydro-3H-1,4-benzodiazepin-2,5-dione and N-methylpiperazine as described in Steps 1C–G. The title compound was obtained as a colourless solid, mp>133° C. (dec.). $R_f$ 0.45 in 10% methanol/dichloromethane on silica plates. ¹H NMR (360 MHz, CDCl₃) δ0.77 (3H, t, J=7 Hz), 1.35–1.57 (2H, m), 2.29 (3H, s), 2.34 (3H, s), 2.35–2.45 (2H, m), 2.45–2.60 (2H, m), 3.18–3.38 (4H, m), 3.51–3.59 (1H, m), 4.31–4.40 (1H, m), 5.25 (1H, d, J=8 Hz), 6.51 (1H, d, J=8 Hz), 6.76 (1H, s), 6.84 (1H, d, J=8 Hz), 7.08–7.56 (7H, m). Found: C, 64.41; H, 7.13; N, 17.95. $C_{25}H_{32}N_6O_2 \cdot H_2O$ requires C, 64.36; H, 7.35; N, 18.01%.

EXAMPLE 9

N-[3(R,S)-2,3-Dihydro-1-methyl-2-oxo-5-(piperazin-1-yl)-1H-1,4-benzodiazepin-3-yl]-N'-[3-methylphenyl]urea Step A: N-[3(R,S)-5-(4-t-Butyloxycarbonylpiperazin-1-yl)-2,3-dihydro-1-methyl-2-oxo-1H -1,4-benzodiazepin-3-yl]-N'-[3-methylphenyl]urea Carrying out Steps 1A–G whilst replacing piperidine in Step 1D with t-butyl 1-piperazine-carboxylate afforded the title compound as a grey solid. mp 246°–248° C. $R_f$ 0.70 in 10% methanol/dichloromethane on silica plates. Found: C, 61.12; H, 6.80; N, 15.47. $C_{27}H_{34}N_6O_4 \cdot 1.25H_2O$ requires C, 61.29; H, 6.95; N, 15.88.

Step B: N-[3(R,S)-2,3-Dihydro-1-methyl-2-oxo-5-(piperazin-1-yl)-1H-1,4-benzodiazepin-3-yl]-N'-[3-methylphenyl]urea Trifluoroacetic acid (0.3 ml) was added to a stirred solution of N-[3(R,S)-5-(4-t-butyloxycarbonylpiperazin-1-yl)-2,3-dihydro-1-methyl-2-oxo-1H-1,4-benzodiazepin-3-yl]-N'-[3-methylphenyl]urea (320 mg) in dichloromethane (15 ml). After stirring for 20 hours further trifluoroacetic acid (0.3 ml) was added. The solution was stirred for 5 days then the solvent was evaporated. The resulting foam was dissolved in water, basified to pH=12 with potassium carbonate then extracted with dichloromethane. The combined organic extracts were dried (sodium sulphate) then evaporated and the crude product recrystallised from ethanol (150 mg). mp 146° C. $R_f$ 0.21 in methanol/dichloromethane on neutral alumina plates. ¹H (360 MHz, DMSO-d₆) δ2.21 (3H, s), 2.60–2.72 (2H, m), 2.74–2.86 (2H, m), 3.00–3.18 (4H, m), 3.33 (3H, s), 4.95 (1H, d, J=8.5 Hz), 7.02 (1H, d, J=8.5 Hz), 6.68–6.72 (8H, m), 8.80 (1H, s). Found: C, 63.30; H, 6.63; N, 20.02. $C_{22}H_{26}N_6O_2 \cdot 0.5H_2O$ requires 63.59; H, 6.55; N, 20.23%.

EXAMPLE 10

N-[3(R,S)-2,3-Dihydro-1-methyl-5-(4-methylpiperazin-1-yl)-2-oxo-1H-1,4-benzodiazepin-3-yl]-N'-[3-methoxyphenyl]urea Step A: 3-Amino-1,2-dihydro-1-methyl-5-(4-methylpiperazin-1-yl)-3H-1,4-benzodiazepin-2-one Trifluoroacetate 1,2-Dihydro-1-methyl-5-(4-methylpiperazin-1-yl)-3-oximido-3H-1,4-benzodiazepin-2-one (Example 4, prepared using the procedure described in Example 1, 250 mg) was dissolved in glacial acetic acid (10 ml). Trifluoroacetic acid (0.13 ml) was added and the solution warmed to 40° C. Zinc granules (130 mg) were added and the mixture was stirred at 40° C. for 5 hours. The mixture was cooled, evaporated to dryness and azeotroped with toluene to afford the crude amine trifluoroacetate salt, which was used in the next step.

Step B: N-[3(R,S)-2,3-Dihydro-1-methyl-5-(4-methylpiperazin-1-yl)-2-oxo-1H-1,4-benzodiazepin-3-yl]-N'-[3-methoxyphenyl]urea The title compound was obtained (185 mg) from the preceding amine free base (obtained from the trifluoroacetate salt) and m-methoxyphenyl isocyanate using the procedure described in Example 1. mp>186° C. (dec.). $R_f$ 0.35 in dichloromethane/methanol (9:1) on silica plates. $^1$H NMR (360 MHz, CDCl$_3$) δ2.32 (3H, s), 2.32–2.60 (4H, m), 3.20–3.40 (4H, m), 3.43 (3H, s), 3.77 (3H, s), 5.27 (1H, d, J=8 Hz), 6.51 (1H, d, J=8 Hz), 6.58 (1H, dd, J$_1$=2 Hz, J$_2$=8 Hz), 6.79 (1H, d, J=8 Hz), 6.87 (1H, s), 7.09–7.56 (6H, m). Found: C, 61.23; H, 6.37; N, 18.40. C$_{23}$H$_{28}$N$_6$O$_3$.0.75H$_2$O requires C, 61.38; H, 6.61; N, 18.67%.

EXAMPLE 11

N-[3(R,S)-2,3-Dihydro-1-methyl-5-(4-methylpiperazin-1-yl)-2-oxo-1H-1,4-benzodiazepin-3-yl]-N/-[3-hydroxyphenyl]urea To a stirred, cooled (−50° C.) solution of N-[3(R,S)-2,3-dihydro-1-methyl-5-(4-methylpiperazin-1-yl)-2-oxo-1H-1, 4-benzodiazepin-3-yl]-N'-[3-methoxyphenyl]urea (130 mg) was added a 1M dichloromethane solution of boron tribromide (1.5 ml), dropwise. The reaction mixture was allowed to warm to 0° C. then stirred at this temperature for 2 hours. Methanol (0.5 ml) was added, solid filtered off and dissolved in water (10 ml). This solution was basified (pH~8) with potassium carbonate then extracted with dichloromethane (3×20 ml). The combined organics were dried (sodium sulphate) then evaporated to give a beige solid (82 mg) which was purified by column chromatography on silica using CH$_2$Cl$_2$/MeOH (10:1)→(7:1), gradient elution. The required product was obtained as a cream solid (48 mg) which was recrystallised from ethyl acetate. mp 187°–189° C. (dec.). $R_f$ 0.14 in dichloromethane/methanol (9:1) on silica plates. MS, CI$^+$, m/z=423 for (M+H)$^+$. Found: C, 59.10; H, 5.82; N, 17.79. C$_{22}$H$_{26}$N$_6$O$_3$.0.2 C$_4$H$_8$O$_2$.1.25H$_2$O requires C, 59.19; H, 6.55; N, 18.16%.

EXAMPLE 12

N-[3(R,S)-2,3-Dihydro-5-(4-methylpiperazin-1-yl)-2-oxo-1-propyl-1H-1,4-benzodiazepin-3-yl]-N'-[3-methoxyphenyl]urea Step A: 3-Amino-1,2-dihydro-5-(4-methylpiperazin-1-yl)-1-propyl-3H-1,4-benzodiazepin-2-one Acetate 1,2-Dihydro-5-(4-methylpiperazin-1-yl)-3-oximido-1-propyl-3H-1,4-benzodiazepin-2-one (Example 8, prepared using the procedure described in Example 1, 120 mg) was hydrogenated at 40 psi in methanol (50 ml), containing glacial acetic acid (21 μL), at 60° C. over 5% rhodium on carbon (112 mg) for 3 hours. The reaction mixture was filtered and evaporated to dryness to afford the crude amine acetate salt which was used in the next step.

Step B: N-[3(R,S)-2,3-Dihydro-5-(4-methylpiperazin-1-yl)-2-oxo-1-propyl-1H-1,4-benzodiazepin-3-yl]-N'-[3-methoxyphenyl]urea The title compound was obtained from the preceding amine free base (obtained from the acetate salt) and m-methoxyphenyl isocyanate using the procedure described in Example 1. mp>180° C. (dec.). $R_f$ 0.30 in 10% methanol/dichloromethane on silica plates. Found: C, 61.30; H, 6.98; N, 16.87. C$_{25}$H$_{32}$N$_6$O$_3$. 1.5H$_2$O requires C, 61.08; H, 7.18; N, 17.10%.

EXAMPLE 13

N-[3(R,S)-2,3-Dihydro-1-methyl-2-oxo-5-(4-methylpiperazin-1-yl)-1H-1,4-benzodiazepin-3-yl]-N'-[3-(2-methyltetrazol-5-yl)phenyl]urea Step A: 5-(3-Nitrophenyl)tetrazole To a solution of 3-cyanonitrobenzene (20 g) in 1-methyl-2-pyrrolidinone (200 ml) was added triethylamine hydrochloride (27.9 g) followed by sodium azide (26.4 g). The mixture was heated at 160° C. for 1.5 hours, then cooled to ambient temperature, poured into ice water (1000 ml) and acidified using 5M HCl. The solid which precipitated from the mixture was filtered, washed with water and dried under vacuum at 50° C. to afford the title tetrazole (22.1 g) as a beige powder. mp 154°–156° C. $^1$H NMR (360 MHz, CDCl$_3$) δ7.59 (1H, dd, J=8 Hz), 8.19 (1H, d, J=8 Hz), 8.36 (1H, d, J=8 Hz), 8.86 (1H, s).

Step B: 1-Methyl-5-(3-nitrophenyl)tetrazole and 2-methyl-5-(3-nitrophenyl)tetrazole Sodium hydroxide (1.22 g) in water (20 ml) was added to a stirred solution of 5-(3-nitrophenyl)tetrazole (5.28 g) in ethanol (60 ml). Iodomethane (1.9 ml) was added and the reaction mixture was stirred at room temperature for 7 hours. Further iodomethane (1.9 ml) was added and the reaction mixture was stirred for a further 18 hours. The mixture was evaporated to dryness and the residue partitioned between ethyl acetate (100 ml) and water (50 ml). The organic layer was separated and the aqueous re-extracted with ethyl acetate (2×100 ml). The combined organics were dried (sodium sulphate) then evaporated to give a brown solid (4.95 g) which was purified by column chromatography on silica using dichloromethane/methanol (10:1) to first afford 2-methyl-5-(3-nitrophenyl)tetrazole (3.85 g) as a cream solid, mp 105° C. $R_f$ 0.78 in dichloromethane/diethyl ether (5:1) on silica plates. $^1$H NMR (360 MHz, CDCl$_3$) δ4.45 (3H, s), 7.70 (1H, dd, J$_1$=J$_2$=8 Hz), 8.33 (1H, ddd, J$_1$=J$_2$=2 Hz, J$_3$=8 Hz), 8.49 (1H, broad d, J=8 Hz), 8.99 (1H, dd, J$_1$=J$_2$=2 Hz). Found: C, 47.12; H, 3.49; N, 34.05. C$_8$H$_7$N$_5$O$_2$ requires C, 46.83; H, 3.44; N, 34.13%.

The second product to elute was 1-methyl-5-(3-nitrophenyl)tetrazole (345 mg) as a cream solid, mp 143°–144° C. $R_f$ 0.60 in dichloromethane/diethyl ether (5:1) on silica plates. $^1$H NMR (360 MHz, CDCl$_3$) δ4.28 (3H, s), 7.82 (1H, dd, J$_1$=J$_2$=8 Hz), 8.18 (1H, ddd, J$_1$=J$_2$=2 Hz, J$_3$=8 Hz), 8.47 (1H, broad d, J=8 Hz), 8.64 (1H, dd, J1=J$_2$=2 Hz). Found: C, 46.96; H, 3.40; N, 34.00. C$_8$H$_7$N$_5$O$_2$ requires C, 46.83; H, 3.44; N, 34.13%.

Step C: 5-(3-Aminophenyl)-2-methyltetrazole

2-Methyl-5-(3-nitrophenyl)tetrazole (2.30 g) was hydrogenated at 20 psi in ethanol (50 ml) using 10% palladium on carbon (230 mg) for 15 minutes. The mixture was filtered then evaporated to dryness in vacuo to give the title compound as a colourless solid (1.55 g), mp 97° C. $R_f$ 0.40 in dichloromethane/methanol (5:1) on silica plates. $^1$H NMR (360 MHz, CDCl$_3$) δ3.80 (2H, broad resonance), 4.38 (3H, s), 6.78 (1H, ddd, J$_1$=J$_2$=8 Hz, J$_3$=8 Hz), 7.26 (1H, dd, J$_1$=J$_2$=8 Hz), 7.47 (1H, dd, J$_1$=J$_2$=2 Hz), 7.51 (1H, dd, J$_1$=2 Hz, J$_2$=8 Hz).

Step D: N-[3(R,S)-2,3-Dihydro-1-methyl-2-oxo-5-(4-methylpiperazin-1-yl)-1H-1,4-benzodiazepin-3-yl]-N'-[3-(2-methyltetrazol-5-yl)phenyl]urea Triphosgene (237 mg) was added to a stirred, cooled (4° C.) solution of 5-(3-Aminophenyl)-2-methyltetrazole (418 mg) in anhydrous tetrahydrofuran (10 ml). Triethylamine (333 μl) was added, the cooling bath was removed and the reaction mixture stirred at room temperature for 40 minutes. A solution of 3-amino-1,2-dihydro-1-methyl-5-(4-methylpiperazin-1-yl)-3H-1,4-benzodiazepin-2-one (Example 4, 572 mg) in anhydrous tetrahydrofuran (10 ml) was added then the reaction mixture was stirred for 3 hours. The solvent was evaporated then the residue was partitioned between water (50 ml) and ethyl acetate (80 ml). The organic layer was separated and the aqueous re-extracted with ethyl acetate (2×80 ml). The combined organics were washed with brine (50 ml) then evaporated and the crude product purified by column chromatography on silica using dichloromethane—10% methanol/dichloromethane (gradient). The required product was triturated with diethyl ether to afford a colourless solid (50 mg), mp>225° C. (dec.). $R_f$ 0.30 in 10% methanol/dichloromethane on silica plates. $^1$H NMR (360 MHz, CDCl$_3$) δ2.32 (3H, s), 2.34–2.44 (2H, m), 2.46≧2.52 (2H, m), 3.20–3.45 (4H, m), 3.45 (3H, s), 4.34 (3H, s), 5.33 (1H, d, J=8 Hz), 6.64 (1H, d, J=8 Hz), 7.26–7.39 (4H, m), 7.51–7.62 (3H, m), 7.75 (1H, d, J=8 Hz), 8.00 (1H, dd, $J_1=J_2=2$ Hz). Found: C, 55.53; H, 5.43; N, 25.81. $C_{24}H_{28}N_{10}O.2.0H_2C_4H_{10O}.2.0H_2O$ requires C, 55.38; H, 6.09; N, 26.04%.

EXAMPLE 14

N-[3(R,S)-2,3-Dihydro-1-methyl-2-oxo-5-(4-methylpiperazin-1-yl)-1H-1,4-benzodiazepin-3-yl)-N'-[3-(1-methyltetrazol-5-yl)phenyl]urea Step A: 5-(3-Aminophenyl)-1-methyltetrazole 1-Methyl-5-(3-nitrophenyl)tetrazole (Example 13, 350 mg) was hydrogenated at 20 psi in ethanol (30 ml) using 10% palladium on carbon (35 mg) for 15 minutes. The mixture was filtered then evaporated to dryness in vacuo to give the title compound as a grey solid (220 mg), mp 156°–157° C. $R_f$ 0.23 in dichloromethane/methanol (5:1) on silica plates. $^1$H NMR (360 MHz, CDCl$_3$) δ3.92 (2H, broad resonance), 4.16 (3H, s), 6.86 (1H, ddd, $J_1=J_2=2$ Hz, $J_3=8$ Hz), 7.01 (1H, broad d, J=8 Hz), 7.06 (1H, dd, $J_1=J_2=2$ Hz), 7.32 (1H, dd, $J_1=J_2=8$ Hz).

Step B: N-[3(R,S)-2,3-Dihydro-1-methyl-2-oxo-5-(4-methylpiperazin-1-yl)-1H-1,4-benzodiazepin-3-yl)-N'-[3-(1-methyltetrazol-5-yl)phenyl]urea Triphosgene (122 mg) was added to a stirred, cooled (4° C.) solution of 5-(3-aminophenyl)-1-methyltetrazole (220 mg) in anhydrous tetrahydrofuran (10 ml). Triethylamine (0.175 ml) was added and the mixture was stirred at 4° C. for 20 minutes. 3-Amino-1,2-dihydro-1-methyl-5-(4-methylpiperazin-1-yl)-3H-1,4-benzodiazepin-2-one trifluoroacetate (Example 10, 650 mg crude) was suspended in anhydrous tetrahydrofuran (10 ml). Triethylamine (0.145 ml) was added and the resulting red solution was added to the pre-formed isocyanate at 4° C. After addition the cooling bath was removed and the mixture stirred at room temperature for 1 hour. The title compound was isolated as described in Example 13 then recrystallised from propan-2-ol to afford a colourless solid (40 mg), mp>210° C. (dec.). $R_f$ 0.30 in dichloromethane/methanol (9:1) on silica plates. Found: C, 55.94; H, 6.52; N, 26.12. $C_{24}H_{28}N_{10}O_2.0.2C_3H_8O.1.5H_2O$ requires C, 55.90; H, 6.40; N, 26.50%.

EXAMPLE 15

N-[3(R,S)-2,3-Dihydro-1-methyl-2-oxo-5-(4-methylpiperazin-1-yl)-1H-1,4-benzodiazepin-3-yl]-N'[3-(N,N-dimethylcarboxamido)phenyl]urea Step A: N,N-Dimethyl-3-nitrophenylcarboxamide Dimethylamine gas was bubbled through a solution of 3-nitrobenzoyl chloride (8.0 g) in dichloromethane (80 ml) for 30 minutes. The solution was washed with water (2×40 ml), dried (sodium sulphate) then evaporated to give a cream solid (8.30 g), mp 83°–85° C. $R_f$ 0.37 in ethyl acetate on silica plates. Found: C, 55.73; H, 5.20; N, 14.29. $C_9H_{10}N_2O_3$ requires C, 55.67; H, 5.19; N, 14.43%.

Step B: 3-(N,N-Dimethylcarboxamido)aniline

N,N-Dimethyl-3-nitrophenylcarboxamide (6.00 g) was hydrogenated at 40 psi in ethanol (150 ml) using 10% palladium on carbon (0.60 g) for 30 minutes. The reaction mixture was filtered, evaporated to give a colourless solid (5.05 g), mp 86°–87° C. $R_f$ 0.22 in ethyl acetate on silica. Found: C, 66.06; H, 7.26; N, 17.28. $C_9H_{12}N_2O$ requires C, 65.83; H, 7.37; N, 17.06%.

Step C: N-[3(R,S)-2,3-Dihydro-1-methyl-2-oxo-5-(4-methylpiperazin-1-yl)-1H -1,4-benzodiazepin-3-yl]-N'-[3-(N,N-dimethylcarboxamido)phenyl]urea The title compound was obtained (88 mg) from 3-(N,N-dimethylcarboxamido)aniline and 3-amino-1,2-dihydro-1-methyl-5-(4-methylpiperazin-1-yl)-3H-1,4-benzodiazepin-2-one trifluoroacetate as described in Example 14. mp 172°–174° C. (dec.). $R_f$ 0.37 in dichloromethane/methanol (5:1) on silica plates. $^1$H NMR (360 MHz, CDCl$_3$) δ2.32 (3H, s), 2.33–2.40 (2H, m), 2.42–2.58 (2H, m), 2.95 (3H, s), 3.08 (3H, s), 3.18–3.40 (4H, m), 3.44 (3H, s), 5.27 (1H, d, J=8 Hz), 6.63 (1H; d, J=8 Hz), 7.02 (1H, d, J=8 Hz), 7.21–7.56 (8H, m). Found: C, 60.30; H, 6.43; N, 19.15. $C_{25}H_{31}N_7O_3.1.3H_2O$ requires C, 59.94; H, 6.76; N, 19.57%.

EXAMPLE 16

N-[3(R,S)-2,3-Dihydro-5-(homopiperazin-1-yl)-1-methyl-2-oxo-1H-1,4-benzodiazepin-3-yl]-N'-[3-methylphenyl]urea Step A: N-[3(R,S)-5-(4-t-Butyloxycarbonylhomopiperazin-1-yl)-2,3-dihydro-1-methyl-2-oxo-1H-1,4-benzodiazepin-3-yl]-N'-[3-methylphenyl]urea Carrying out Steps 1A–G whilst replacing piperidine in Step 1D with t-butyl-1-homopiperazine-carboxylate afforded the title compound as a semi-solid. $^1$H NMR (360 MHz, CDCl$_3$) δ1.44 (9H, s), 1.58–1.63 (2H, m), 2.29 (3H, s), 3.20–3.60 (8H, m) overlapped with 3.41 (3H, s), 5.26 (1H, d, J=8 Hz), 6.34–6.38 (1H, m), 6.75–7.53 (9H, m).

Step B: N-[3(R,S)-2,3-Dihydro-5-(homopiperazin-1-yl)-1-methyl-2-oxo-1H-1,4-benzodiazepin-3-yl]-N'-[3-methylphenyl]urea The title compound was obtained (230 mg) from the preceding compound (Step A) and trifluoroacetic acid as described in Example 9. mp 182°–185° C. (ethanol). $R_f$ 0.42 in 10% methanol/dichloromethane on neutral alumina plates. $^1$H NMR (360 MHz, CDCl$_3$) δ1.50–1.92 (2H, m), 2.29 (3H, s), 2.70–3.10 (4H, m), 3.42 (3H, s), 3.44–3.60 (4H, m), 5.25 (1H, d, J=8 Hz), 6.40 (1H, d, J=8 Hz), 6.80–7.57 (9H, m). Found: C, 65.54; H, 6.59; N, 19.85. $C_{23}H_{28}N_6O_2$ requires C, 65.69, H, 6.71; N, 19.99%.

EXAMPLE 17

N-[3(R,S)-2,3-Dihydro-1-methyl-5-(4-methylhomopiperazin-1-yl)2-oxo-1H-1,4-benzodiazepin-3-yl]-N'-[3-methylphenyl]urea N-[3(R,S)-2,3-Dihydro-5-(homopiperazin-1-yl)-1-methyl-2-oxo-1H-1,4-benzodiazepin-3-yl]-N'-[3-methylphenyl]urea (Example 16, 70 mg) was dissolved in methanol (8 ml) and treated with sodium cyanoborohydride (21 mg) followed by glacial acetic acid (42 µl) then formaldehyde (34 µl of a 38% w/v solution). The reaction mixture was stirred at room temperature for 1 hour then was evaporated to dryness. The resulting solid was partitioned between saturated aqueous sodium carbonate and dichloromethane. The organic layer was separated and the aqueous re-extracted with dichloromethane. The combined organics were dried (sodium sulphate) then evaporated to afford the title compound (73 mg). mp 190°–192° C. (ethanol). $R_f$ 0.80 in 10% methanol/dichloromethane on neutral alumina plates. $^1$H NMR (360 MHz, CDCl$_3$) δ1.75–2.04 (2H, m), 2.29 (3H, s), 2.34 (3H, s), 2.48–2.74 (4H, m), 3.42 (3H, s), 3.44–3.66 (4H, m), 5.23 (1H, d, J=8 Hz), 6.37 (1H, d, J=8 Hz), 6.75–7.58 (9H, m). Found: C, 66.30; H, 6.86; N, 19.11. $C_{24}H_{30}N_6O_2$ requires C, 66.34; H, 6.96; N, 19.34%.

EXAMPLE 18

N-[3(R,S)-2,3-Dihydro-1-methyl-2-oxo-5-(4-methylpiperazin-1-yl)-1H-1,4-benzodiazepin-3-yl]-N'-[3-(N-ethylcarboxamido)phenyl]urea Step A: N-Ethyl-3-nitrophenylcarboxamide Ice cold ethylamine (33 ml) was added dropwise from a dropping funnel to a stirred, cooled (0° C.) solution of 3-nitrobenzoyl chloride (10.0 g) in anhydrous dichloromethane (100 ml). After addition the cooling bath was removed and the reaction mixture was stirred at room temperature for 1 hour. The solution was washed with water (2×50 ml), dried (sodium sulphate) then evaporated to give a solid which was recrystallised from dichloromethane/n-hexane to give the title compound as a colourless crystalline solid (10.10 g). mp 122°–123° C. $R_f$ 0.44 in ethyl acetate on silica plates. Found: C, 56.11; H, 5.23; N, 14.62. $C_9H_{10}N_2O_3$ requires C, 55.67; H, 5.19; N, 14.43%.

Step B: 3-(N-Ethylcarboxamido)aniline

N-Ethyl-3-nitrophenylcarboxaamide (7.0 g) was hydrogenated at 40 psi in ethanol (180 ml) using 10% palladium on carbon (0.70 g) for 30 minutes. The reaction mixture was filtered, evaporated to give a grey viscous gum (5.62 g). $R_f$ 0.32 in ethyl acetate on silica plates. Found: C, 65.19; H, 7.33; N, 16.81. $C_9H_{12}N_2O$ requires C, 65.83; H, 7.37; N, 17.06%.

Step C: N-[3(R,S)-2,3-Dihydro-1-methyl-2-oxo-5-(4-methylpiperazin-1-yl)-1H-1,4-benzodiazepin-3-yl]-N'-[3-(N-ethylcarboxamido)phenyl]urea The title compound was obtained (130 mg) from 3-(N-ethylcarboxamido)aniline and 3-amino-1,2-dihydro-1-methyl-5-(4-methylpiperazin-1-yl)-3H-1,4-benzodiazepin-2-one trifluoroacetate as described in Example 14. mp 161°–164° C. $R_f$ 0.45 in dichloromethane/methanol (5:1) on silica plates. $^1$H NMR (360 MHz, CDCl$_3$) δ1.20 (3H, t, J=7 Hz), 2.31 (3H, s), 2.31–2.60 (4H, m), 3.20–3.40 (4H, m), 3.39–3.47 (2H, m), 3.45 (3H, s), 5.30 (1H, d, J=8 Hz), 6.56 (1H, broad t, J=5 Hz), 6.79 (1H, d, J=8 Hz), 7.22–7.68 (9H, m). Found: C, 58.43; H, 6.35; N, 18.53. $C_{25}H_{31}N_7O_3 \cdot 2H_2O \cdot 0.1C_4H_{10}O$ requires C, 58.55; H, 6.86; N, 18.82%.

EXAMPLE 19

N-[3(R,S)-2,3-Dihydro-1-methyl-2-oxo-5-(piperidin-1-yl)-1H-1,4-benzodiazepin-3-yl]-N'-[3-ethylphenyl] urea Step A: 3-Amino-1,2-dihydro-1-methyl-5-(piperidin-1-yl)-3H-1,4-benzodiazepin-2-one A suspension of 1,2-dihydro-1-methyl-3-oximido-5-(piperidin-1-yl)-3H-1,4-benzodiazepin-2-one (400 mg) and 5% rhodium on carbon (400 mg) in methanol (40 ml) was hydrogenated at 40 psi at 60° C. for 5 hours. The reaction mixture was filtered then evaporated to dryness to afford the title compound as a beige gum (380 mg).

Step B: N-[3(R,S)-2,3-Dihydro-1-methyl-2-oxo-5-(piperidin-1-yl)-1H-1,4-benzodiazepin-3-yl]-N'-[3-ethylphenyl]urea A solution of m-ethylphenyl isocyanate (206 mg) in anhydrous tetrahydrofuran (3 ml) was added to a cooled (4° C.) solution of 3-amino-1,2-dihydro-1-methyl-5-(piperidin-1-yl)-3H-1,4-benzodiazepin-2-one (380 mg) in anhydrous tetrahydrofuran (5 ml) and the reaction mixture was left standing at 4° C. for 1 hour. The reaction mixture was evaporated to dryness then the residue was partitioned between ethyl acetate (30 ml) and water (20 ml). The organic layer was separated, aqueous re-extracted with ethyl acetate (2×30 ml). The combined organics were dried (sodium sulphate) then evaporated to give a beige gum which was purified by column chromatography-on silica using dichloromethane/methanol (30:1) to afford the title compound as a colourless solid (320 mg). mp 222°–223° C. (methanol). $R_f$ 0.61 in dichloromethane/methanol (9:1) on silica plates. Found: C, 66.11; H, 6.90; N, 16.04. $C_{24}H_{29}N_5O_2 \cdot 1H_2O$ requires C, 65.88; H, 7.14; N, 16.01%.

EXAMPLE 20

N-[3(R,S)-2,3-Dihydro-5-(homopiperidin-1-yl)-1-methyl-2-oxo-1H-1,4-benzodiazepin-3-yl]-N'-[3-methylphenyl]urea Step A: 1,2-Dihydro-5-(homopiperidin-1-yl)-1-methyl-3-oximido-3H-1,4-benzodiazepin-2-one Carrying out Steps 1A–1E whilst replacing piperidine in Step 1D with homopiperidine afforded the title compound as a cream solid (0.77 g). mp 210°–212° C. (ethyl acetate/diethyl ether). MS, CI$^+$, m/z 301 for (M+H)$^+$. Found: C, 64.09; H, 6.60; N, 17.92. $C_{16}H_{20}N_4O_2$ requires C, 63.98; H, 6.71; N, 18.65%.

Step B: 3-Amino-1,2-dihydro-5-(homopiperidin-1-yl)-1-methyl-3H-1,4-benzodiazepin-2-one The title compound was obtained (372 mg) from the preceding oxime (400 mg) using 5% rhodium on carbon (400 mg) as described in Example 19.

Step C: N-[3(R,S)-2,3-Dihydro-5-(homopiperidin-1-yl)-1-methyl-2-oxo-1H-1,4-benzodiazepin-3-yl]-N'-[3-methylphenyl]urea The title compound was obtained (220 mg) from 3-amino-1,2-dihydro-5-(homopiperidin-1-yl)-1-methyl-3H-1,4-benzodiazepin-2-one and m-tolyl isocyanate as described in Example 19. mp 210°–211° C. (methanol). $R_f$ 0.63 in dichloromethane/methanol (9:1) on silica plates. Found: C, 69.16; H, 7.00; N, 16.89. $C_{24}H_{29}N_5O_2$ requires C, 68.71; H, 6.97; N, 16.69%.

EXAMPLE 21

N-[3(R,S)-2,3-Dihydro-5-(4-methylpiperazin-1-yl)-2-oxo-1-propyl-1H-1,4-benzodiazepin-3-yl ]-N'-[3-ethylphenyl]urea The title compound was obtained (140 mg) from 3-amino-1,2-dihydro-5-(4-methylpiperazin-1-yl)-1-propyl-3H-1,4-benzodiazepin-2-one trifluoroacetate (prepared using the procedure described in Example 10) and m-ethylphenyl isocyanate. mp 203°–204° C. (ethyl acetate). $R_f$ 0.40 in 10% methanol/dichloromethane on silica plates. Found: C, 66.06; H, 7.46; N, 17.84. $C_{26}H_{34}N_6O_2 \cdot 0.5H_2O$ requires C, 66.22; H, 7.48; N, 17.82%.

EXAMPLE 22

N-[3(R,S)-2,3-Dihydro-5-(4-methylpiperazin-1-yl)-1-(2-methylpropyl)-2-oxo-1H-1,4-benzodiazepin-3-yl]-N'-[3-methylphenyl]urea Step A: Methyl N-(2-methylpropyl)anthranilate The title compound was obtained from methyl anthranilate and isobutyraldehyde as described in Example 8. bp 145° C. (0.3 mmHg) (Kugelrohr). $R_f$ 0.75 in ethyl acetate/n-hexane (1:1) on silica plates.

Step B: 1-(2-Methylpropyl-1,2,3,4-tetrahydro-3H-1,4-benzodiazepin-2,5-dione

Prepared from methyl N-(2-methylpropyl)anthranilate using the method described in Example 1. mp 176°–178° C. (dichloromethane/diethyl ether). Found: C, 67.35; H, 6.74; N, 12.13. ($C_{13}H_{16}N_2O_2$ requires C, 67.22; H, 6.94; N, 12.06%.

Step C: 1,2-Dihydro-5-(4-methylpiperazin-1-yl)-1-(2-methylpropyl)-3H-1,4-benzodiazepin-2-one Prepared from 1-(2-methylpropyl)-1,2,3,4-tetrahydro-3H-1,4-benzodiazepin-2,5-dione and N-methylpiperazine using the method described in Example 1 (Steps C and D). mp 134°–136° C. (dichloromethane/diethyl ether). Found: C, 68.98; H, 8.40; N, 17.92. $C_{18}H_{26}N_4O$ requires C, 68.76; H, 8.33; N, 17.82%.

Step D: N-[3(R,S)-2,3-Dihydro-5-(4-methylpiperazin-1-yl)-1-(2-methylpropyl)-2-oxo-1H-1,4-benzodiazepin-3-yl]-N'-[3-methylphenyl]urea The title compound was obtained using the procedures described in Example 1 (Step E) and Example 10 (Steps A and B). mp 220°–222° C. (ethyl acetate/n-hexane). $R_f$ 0.35 in 10% methanol/dichloromethane on silica plates; $^1$H NMR (360 MHz, CDCl$_3$) δ 0.72 (3H, d, J=7 Hz), 0.78 (3H, d, J=7 Hz), 1.60–1.80 (1H, m), 2.30 (3H, s), 2.32 (3H, s), 2.30–2.60 (4H, m), 3.18–3.40 (4H, m), 3.37 (1H, dd, $J_1$=5, $J_2$=14 Hz), 4.31 (1H, dd, $J_1$=9, $J_2$=14 Hz), 5.25 (1H, d, J=8 Hz), 6.49 (1H, d, J=8 Hz), 6.71 (1H, s), 6.84–7.60 (8H, m). Found: C, 67.63; H, 7.26; N, 18.29. $C_{26}H_{34}N_6O_2$ requires C, 67.51; H, 7.41; N, 18.17%.

EXAMPLE 23

N-[3(R,S)-2,3-Dihydro-5-(4-methylpiperazin-1-yl)-1-(2-methylpropyl)-2-oxo-1H-1,4-benzodiazepin-3-yl]-N'-[3-ethylphenyl]urea The title compound was obtained as described in Example 22, using m-ethylphenyl isocyanate in the final step. mp 223°–224° C. (ethyl acetate/n-hexane). $R_f$ 0.36 in 10% methanol/dichloromethane on silica plates. Found: C, 68.44; H, 7.64; N, 17.81. $C_{27}H_{36}N_6O_2$ requires C, 68.04; H, 7.61; N, 17.63%.

EXAMPLE 24

(−)-N-(2,3-Dihydro-5-(4-methylpiperazin-1-yl)-2-oxo-1-propyl-1H-1,4-benzodiazepin-3-yl]-N'-[3-methylphenyl]urea N-(3(R,S)-2,3-Dihydro-5-(4-methylpiperazin-1-yl)-2-oxo-1-propyl-1H-1,4-benzodiazepin-3-yl]-N'-[3-methylphenyl]urea (Example 8) was separated into its two enantiomers using a semi-preparative dinitrobenzoylleucine 5μ column [(250×8)mm] eluting with 1% methanol in dichloromethane (including 0.8% acetic acid). Flow rate=4 ml/minute, U.V. detection at 310 nm. Analysis was performed on an analytical dinitrobenzoylleucine 5μ column[ (250×4.6)mm] eluting with 5% methanol in dichloromethane (including 0.4% acetic acid). Flow rate=1 ml/minute, U.V. detection at 250 nm.

The free base was liberated and obtained as a cream powder (227 mg). HPLC $R_t$=4.3 minutes. $[\alpha]^{23°}$ $^C_D$=−61.5° (c=0.2, methanol). The L-tartrate salt had mp>160° C. (dec) (ethanol).

EXAMPLE 25

(+)-N-(2,3-Dihydro-5-(4-methylpiperazin-1-yl)-2-oxo-1-propyl-1H-1,4-benzodiazepin-3-yl]-N'-[3-methylphenyl]urea The title compound free base was obtained (188 mg) using the procedure described in Example 24. HPLC-$R_t$=8.3 minutes. $[\alpha]^{23°}$ $^C_D$=+66.5° (c=0.2, methanol). The L-tartrate salt had mp>157° C. (dec) (ethanol).

EXAMPLE 26

(−)-N-[2,3-Dihydro-5-(4-methylpiperazin-1-yl)-1-(2-methylpropyl)-2-oxo-1H-1,4-benzodiazepin-3-yl]-N'-[3-ethylphenyl]urea N-[3(R,S)-2,3-Dihydro-5-(4-methylpiperazin-1-yl)-1-(2-methylpropyl)-2-oxo-1H-1,4-benzodiazepin-3-yl]-N'-[3-ethylphenyl]urea (Example 23, 700 mg) was separated into its two enantiomers using a semi-preparative dinitrobenzoylleucine Pirkle column [(250×20)mm] eluting with 2% methanol in dichloromethane (including 0.8% acetic acid). Flow rate=20 ml/minute, U.V. detection at 280 nm. Analysis was performed on an analytical dinitrobenzoylleucine Pirkle column [(250×4.6mm)] eluting with 3% methanol in dichloromethane (including 1% acetic acid). Flow rate=1 ml/minute, U.V. detection at 250 nm.

The free base was liberated and obtained as a cream powder (200 mg). HPLC $R_t$=3.43 minutes. $[\alpha]^{23°}$ $^C_D$=−59.5° (c=0.2, methanol). mp>113° C. (dec.).

EXAMPLE 27

(+)-N-[2,3-Dihydro-5-(4-methylpiperazin-1-yl)-1-(2-methylpropyl)-2-oxo-1H-1,4-benzodiazepin-3-yl]-N'-[3-ethylphenyl]urea The title compound was obtained (270 mg) using the procedure described in Example 26. HPLC $R_t$=5.61 minutes. $[\alpha]^{23°}$ $^C_D$=+50.0° (c=0.2, methanol). mp>113° C. (dec.).

EXAMPLE 28

(−)-N-[2,3-Dihydro-5-(homopiperidin-1-yl)-1-methyl-2-oxo-1H-1,4-benzodiazepin-3-yl]-N'-[3-methylphenyl]urea N-[3(R,S)-2,3-Dihydro-5-(homopiperidin-1-yl)-1-methyl-2-oxo-1H-1,4-benzodiazepin-3-yl]-N'-[3-methylphenyl] urea (Example 20, 500 mg) was separated into its two enantiomers using a semi-preparative dinitrobenzoylleucine Pirkle column (5μ) [(250×20)mm] eluting with 5% methanol in 1-chlorobutane (including 1% acetic acid). Flow rate 20 ml/minute, U.V. detection at 300 nm. Analysis was performed on an analytical dinitrobenzoylleucine Pirkle column (5μ) [(250×4.6)mm] eluting with 5% methanol in 1-chlorobutane. Flow rate 1.5ml/min, U.V. detection at 250 nm.

The free base was liberated and obtained as a colourless solid (186 mg). HPLC $R_t$=4.1 minutes (>99% ee). $[\alpha]^{24°}$ $c_D$=−62.0° (c=0.2, methanol). mp 177°–179° C. The hydrochloride salt had mp 201°–204° C. (acetone/ethyl acetate (1:1)). $[\alpha]^{24°}$ $^C_D$=−139.5° (c=0.2, methanol); $^1$H NMR (360 MHz, D$_2$O) δ 1.36–2.08 (8H, m), 2.30 (3H, s), 3.48 (3H, S), 3.65–3.72 (4H, m), 5.54 (1H, s), 7.01 (1H, d, J=8 Hz), 7.12–7.17 (2H, m), 7.26 (1H, dd, $J_1$=$J_2$=8 Hz), 7.57 (1H, dd, $J_1$=$J_2$=8 Hz), 7.64 (1H, dd, $J_1$=1, $J_2$=8 Hz), 7.78 (1H, dd, $J_1$=1, $J_2$=8 Hz), 7.85 (1H, ddd, $J_1$=1, $J_2$=$J_3$=8 Hz). Found: C, 61.38; H, 6.50; N, 14.82. $C_{24}H_{29}N_5O_2 \cdot HCl \cdot 0.75H_2O$ requires C, 61.40; H, 6.76; N, 14.92%.

EXAMPLE 29

(+)-N-[2,3-Dihydro-5-(homopiperidin-1-yl)-1-methyl-2-oxo-1H-1,4-benzodiazepin-3-yl]-N'-[3-methylphenyl]urea The title compound was obtained (200 mg) using the procedure described in Example 28. HPLC $R_t$=9.9 minutes (99% ee). $[\alpha]^{24°}{}^C{}_D$=+63.5° (c=0.2, methanol). mp 172°–175° C. The hydrochloride salt had mp 195°–199° C. (acetone). $[\alpha]^{24°}{}^C{}_D$=+140.2° (c=0.2, methanol). Found: C, 61.09; H, 6.69; N, 14.43. $C_{24}H_{29}N_5O_2 \cdot HCl \cdot H_2O$ requires C, 60.81; H, 6.81; N, 14.77%.

EXAMPLE 30

N-[3(R,S)-2,3-Dihydro-1-methyl-2-oxo-5-(4-methylpiperazin-1-yl)-1H-1,4-benzodiazepin-3-yl]-N'-[3-trifluoromethylphenyl]urea Step A: 3-Amino-1,2-dihydro-1-methyl-5-(4-methylpiperazin-1-yl)-3H-1,4-benzodiazepin-2-one Trifluoroacetate 1,2-Dihydro-1-methyl-5-(4-methylpiperazin-1-yl)-3-oximido-3H-1,4-benzodiazepin-2-one (Example 4, prepared using the procedure described in Example 1, 320 mg) was dissolved in glacial acetic acid (10 ml). Trifluoroacetic acid (0.16 ml) was added and the solution warmed to 40° C. Activated zinc powder (Fieser and Fieser, 1967, Volume 1, 1276, 166 mg, 2.54 mmol) was added and the mixture was stirred at 40° C. for 3 hours. The mixture was cooled, evaporated to dryness and azeotroped with toluene to afford the crude amine trifluoroacetate salt, which was used in the next step.
Step B: N-[3(R,S)-2,3-Dihydro-1-methyl-2-oxo-5-(4-methylpiperazin-1-yl)-1H-1,4-benzodiazepin-3-yl]-N'-[3-trifluoromethylphenyl]urea The title compound was obtained (382 mg) from the preceding amine free base (obtained from the trifluoroacetate salt) and 3-trifluoromethylphenyl isocyanate using the procedure described in Example 1. mp 248°–250° C. (dec.) (methanol). $R_f$ 0.37 in dichloromethane/methanol (9:1) on silica plates. Found: C, 58.65; H, 5.33; N, 17.92; F, 11.69. $C_{23}H_{25}F_3N_6O_2$ requires C, 58.22; H, 5.31; N, 17.71; F, 12.01%.

EXAMPLE 31

N-[3(R,S)-2,3-Dihydro-1-methyl-2-oxo-5-(4-methylpiperazin-1-yl)-1H-1,4-benzodiazepin-3-yl]-N'-phenyl urea The title compound was obtained (150 mg) from 3-amino-1,2-dihydro-1-methyl-5-(4-methylpiperazin-1-yl)-3H-1,4-benzodiazepin-2-one and phenyl isocyanate using the procedure described in Example 1. mp 148°–150° C. (methanol/diethyl ether). $R_f$ 0.19 in dichloromethane/methanol (9:1) on silica plates. Found: C, 62.67; H, 6.48; N, 20.05. $C_{22}H_{26}N_6O_2 \cdot 0.75H_2O$ requires C, 62.91; H, 6.60; N, 20.01%.

EXAMPLE 32

N-[3(R,S)-2,3-Dihydro-5-(4-methylpiperazin-1-yl)-2-oxo-1-propyl-1H-1,4-benzodiazepin-3-yl]-N'-[3-trifluoromethylphenyl]urea Step A: 3-Amino-1,2-dihydro-5-(4-methylpiperazin-1-yl)-1-propyl-3H-1,4-benzodiazepin-2one Trifluoroacetate 1,2-Dihydro-5-(4-methylpiperazin-1-yl)-3-oximido-1-propyl-3H-1,4-benzodiazepin-2-one (410 mg) was dissolved in glacial acetic acid (10 ml). Trifluoroacetic acid (0.67 ml) was added and the solution warmed to 40° C. Activated zinc powder (Fieser and Fieser, 1967, Volume 1, 1276, 567 mg) was added and the mixture was stirred at 40° C. for 10 hours. The mixture was cooled, filtered then evaporated to dryness and azeotroped with toluene to afford the crude amine trifluoroacetate salt, which was used in the next step.
Step B: N-[3(R,S)-2,3-Dihydro-5-(4-methylpiperazin-1-yl)-2-oxo-1-propyl-1H-1,4-benzodiazepin-3-yl]-N'-[3-trifluoromethylphenyl]urea The title compound was obtained (185 mg) from the preceding amine free base (obtained from the trifluoroacetate salt) and 3-trifluoromethylphenyl isocyanate using the procedure described in Example 1. mp 220°–222° C. (ethyl acetate). $R_f$ 0.20 in dichloromethane/methanol (9:1) on silica plates. Found: C, 59.74; H, 5.97; N, 16.55; F, 11.13. $C_{25}H_{29}F_3N_6O_2$ requires C, 59.75; H, 5.82; N, 16.72; F, 11.34%.

EXAMPLE 33

N-[3(R,S)-2,3-Dihydro-5-(4-methylpiperazin-1-yl)-2-oxo-1-propyl-1H-1,4-benzodiazepin-3-yl]-N'-[5-indanyl]urea Step A: 3-Amino-1,2-dihydro-5-(4-methylpiperazin-1-yl)-1-propyl-3H-1,4-benzodiazepin-2-one Trifluoroacetate 1,2-Dihydro-5-(4-methylpiperazin-1-yl)-3-oximido-1-propyl-3H-1,4-benzodiazepin-2-one (2.0 g) was dissolved in glacial acetic acid (35 ml). Trifluoroacetic acid (4.68 ml) was added and the solution warmed to 40° C. Activated zinc powder (Fieset and Fieser, 1967, Volume 1, 1276, 3.97 g) was added and the mixture was stirred at 40° C. for 5 hours. The mixture was cooled, filtered then evaporated to give the crude amine trifluoroacetate salt, which was used in the next step.

Step B: N-[3(R,S)-2,3-Dihydro-5-(4-methylpiperazin-1-yl)-2-oxo-1-propyl-1H-1,4-benzodiazepin-3-yl]-N'-[5-indanyl]urea The title compound was obtained (65 mg) from the preceding amine free base (obtained from the trifluoroacetate salt), 5-aminoindan and triphosgene as described in Example 14, Step B. mp 170°–171° C. (methanol). $R_f$ 0.30 in dichloromethane/methanol (9:1) on silica plates. $^1$H NMR (360 MHz, CDCl$_3$) δ0.77 (3H, t, J=7 Hz), 1.35–1.55 (2H, m), 2.0–2.1 (2H, m), 2.33 (3H, s), 2.3–2.4 (2H, m), 2.44–2.56 (2H, m), 2.8–2.9 (4H, m), 3.20–3.35 (4H, m), 3.50–3.58 (1H, m), 4.31–4.40 (1H, m), 5.24 (1H, d, J=8 Hz), 6.37 (1H, d, J=8 Hz), 6.44 (1H, s), 7.03 (1H, d, J=8 Hz), 7.13 (1H, d, J=8 Hz), 7.24–7.29 (2H, m), 7.35 (1H, d, J=8 Hz), 7.46–7.55 (2H, m). MS, CI$^+$, m/z=476. Found: C, 65.83; H, 7.37; N, 17.06. $C_{27}H_{34}N_6O_2 \cdot H_2O$ requires C, 6.09; H, 7.16; N, 17.30%.

EXAMPLE 34

(−)-N-[2,3-Dihydro-5-(4-methylpiperazin-1-yl)-2-oxo-1-propyl-1H-1,4-benzodiazepin-3-yl]-N'-[5-indanyl]urea Step A: α-Amino-N-(2,3-dihydro-5-(4-methylpiperazin-1-yl)-2-oxo-1-propyl-1H-1,4-benzodiazepin-3-yl)benzene propanamide To a stirred solution of 3-amino-1,2-dihydro-5-(4-methylpiperazin-1-yl)-1-propyl -3H -1,4-benzodiazepin-2- one (Example 33, 2.96 g) in anhydrous dimethylformamide (30 ml) was added BOC-D-phenylalanine (2.61 g), 1-hydroxybenzotriazole (1.33 g), 1-(3-dimethylaminopropyl)-3-ethyl-carbodiimide hydrochloride (1.89 g) and triethylamine (1.37 ml). After sting at room temperature for 15 minutes the solution was treated with saturated sodium hydrogen carbonate solution then extracted with ethyl acetate (4×100 ml). The combined organics were washed with saturated sodium chloride solution, dried (sodium sulphate), evaporated to dryness and the resulting brown oil purified by column chromatography on silica using 5% methanol/dichloromethane to 10% methanol/dichloromethane. The product obtained (5.28 g) was treated at 0° C. with ethyl acetate (100 ml) saturated with hydrogen chloride gas and stirred at 0° C. for 1 hour. The solution was basified to pH=9 with saturated sodium hydrogen carbonate solution, the organic layer was separated and the aqueous re-extracted with ethyl acetate (4×100 ml). The combined organics were dried (sodium sulphate) and the more polar (by silica tlc) diastereomer crystallised from methanol/diethyl ether to afford a beige solid (460 mg). mp 152°–153° C. Rf 0.50 in dichloromethane/methanol/ammonia (9:1:0.1) on silica plates. HPLC (Spherisorb ODS2 column, 25% acetonitrile/75% of 0.2% triethylamine in water, pH to 3 with orthophosphoric acid): $R_t$ 5.09 minutes, 99.5%. $^1$H NMR (360 MHz, DMSO-$d_6$) δ0.68 (3H, t, J=7 Hz), 1.20–1.29 (1H, m), 1.37–1.44 (1H, m), 2.19 (3H, s), 2.25–2.35 (2H, m), 2.40–2.48 (2H, m), 2.59 (1H, dd, $J_1$=9, $J_2$=13 Hz), 3.00 (1H, dd, $J_1$=4, $J_2$=13 Hz), 3.10–3.30 (4H, m), 3.47 (1H, dd, $J_1$=4 Hz, $J_2$=9 Hz), 3.60–3.68 (1H, m), 4.19–4.28 (1H, m), 4.97 (1H, d, J=8 Hz), 7.16–7.30 (5H, m), 7.36–7.42 (1H, m), 7.55 (1H, d, J=8 Hz), 7.63–7.66 (2H, m), 8.76 (1H, d, J=8 Hz). Found: C, 67.62; H, 7.24; N, 18.17. $C_{26}H_{34}N_6O_2$ requires 67.51; H, 7.41; N, 18.17%.

Step B: (-)-N-[2,3-Dihydro-5-(4-methylpiperazin-1-yl)-2-oxo-1-propyl-1H-1,4-benzodiazepin-3-yl]-N'-[5-indanyl]urea Phenyl isothiocyanate (117 μl) was added to a stirred solution of the foregoing diastereomeric amide (0.41 g) in anhydrous dichloromethane (20 ml) then heated at 40° C. for 3 hours. The reaction mixture was evaporated and the residue purified by column chromatography on silica using dichloromethane to dichloromethane/methanol/ammonia (20:1:0.1), gradient elution, to afford the thiourea (0.53 g). Trifluoroacetic acid (20 ml) was added to the solid thiourea (0.53 g) and the mixture was stirred at room temperature for 40 minutes. The mixture was evaporated to dryness, the residue dissolved in water (50 ml), washed with diethyl ether (20 ml) then the aqueous was freeze dried and azeotroped with toluene to afford the homochiral amine trifluoroacetate (0.54 g) which was used crude.

(-)-N-[2,3-Dihydro-5-(4-methylpiperazin-1-yl)-2-oxo-1-propyl-1H-1,4-benzodiazepin-3-yl]-N'-[5-indanyl]urea was obtained (170 mg) from the foregoing homochiral amine free base (obtained from the trifluoroacetate salt), 5-aminoindan and triphosgene as described in Example 14, Step B, ensuring the mixture was at pH=9. mp>152° C. HPLC (Spherisorb ODS2 column, 50% acetonitrile/50% of 0.2% triethylamine in water, pH to 3 with orthophosphoric acid): $R_t$ 6.9 minutes, >99%. Chiral HPLC (Pirkle dinitrobenzoylleucine column, 3% methanol in dichloromethane (containing 1% acetic acid)): 98.6% ee. $[\alpha]^{23}$ C.$_D$=-71.5° (c=0.2, methanol). Found: C, 68.25; H, 7.16; N, 17.85. $C_{27}H_{34}N_6O_2$ requires C, 68.33; H, 7.22; N, 17.71%.

EXAMPLE 35

N-[3(R,S)-2,3-Dihydro-5-(4-methylpiperazin-1-yl)-2-oxo-1-propyl-1H-1,4-benzodiazepin-3-yl]-N'-[3-propylphenyl]urea Step A: 3-Propylaniline To a stirred, cooled (4° C.) solution of 3-nitrobenzaldehyde (5.0 g), ethyltriphenylphosphonium bromide (14.74 g) and 18-crown-6 (50 mg) in anhydrous dichloromethane (100 ml) was added potassium t-butoxide (4.72 g) over 5 minutes. After addition the reaction mixture was stirred at 4° C. for 30 minutes then at room temperature for 2 hours. 2M Hydrochloric acid (100 ml) was added, the organic layer was separated, washed with water (2×100 ml), dried (sodium sulphate) then evaporated to give an orange gum (15.7 g) which was purified by column chromatography on silica using ethyl acetate/petroleum ether (60–80) [5:1] to afford 3-nitro-propen-1-ylbenzene (5.10 g) as an orange oil. Rf 0.65 in ethyl acetate/n-hexane (1:1) on silica plates. 3-Nitro-propen-1-ylbenzene (5.10 g, 0.0313mol) was hydrogenated at 45 psi over 10% palladium on carbon (500 mg) in ethanol (50 ml) for 20 hours. The reaction mixture was filtered, then evaporated to dryness to give a yellow oil which was distilled under vacuum. 3-Propylaniline (3.40 g) was obtained as a colourless oil. bp 120° C. (0.6 mmHg, Kugelrohr). Rf 0.49 in ethyl acetate/n-hexane (1:1) on silica plates. $^1$H NMR (360 MHz, CDCl$_3$) δ0.93 (3H, t, J=8 Hz), 1.61 (2H, sextet, J=8 Hz), 2.50 (2H, t, J=8 Hz), 3.82 (2H, broad resonance), 6.53–6.62 (3H, m), 7.07 (1H, dd, $J_1$=$J_2$=8 Hz).

Step B: N-[3(R,S)-2,3-Dihydro-5-(4-methylpiperazin-1-yl)-2-oxo-1-propyl-1H-1,4-benzodiazepin-3-yl]-N'-[3-propylphenyl]urea The title compound was obtained (250 mg) from 3-amino-1,2-dihydro-5-(4-methyl piperazin-1-yl)-1-propyl -3H -1,4-benzodiazepin-2-one (obtained from the trifluoroacetate salt), 3-propylaniline and triphosgene as described in Example 14, Step B. mp 200°–201° C. (ethyl acetate/n-hexane). R$_f$ 0.22 in dichloromethane/methanol (9:1) on silica plates. $^1$H NMR (360 MHz, CDCl$_3$) δ0.77 (3H, t, J=7 Hz), 0.91 (3H, t, J=7 Hz), 1.35–1.66 (4H, m), 2.36 (3H, s), 2.36–2.65 (6H, m), 3.20–3.40 (4H, m), 3.51–3.59 (1H, m), 4.31–4.39 (1H, m), 5.25 (1H, d, J=8 Hz), 6.53 (1H, d, J=8 Hz), 6.82–7.54 (9H, m). Found: C, 67.40; H, 7.51; N, 17.80. $C_{27}H_{36}N_6O_2 \cdot 0.25H_2O$ requires C, 67.40; H, 7.65; N, 17.47%.

EXAMPLE 36

N-[3(R,S)-2,3-Dihydro-2-oxo-5-(piperazin-1-yl)-1-propyl-1H-1,4-benzodiazepin-3-yl]-N'-[3-methylphenyl]urea The title compound was obtained (3.07 g) from N-[3(R,S)-5-(4-t-butyloxycarbonylpiperazin-1-yl)-2,3-dihydro-2-oxo-1-propyl-1H-1,4-benzodiazepin-3-yl]-N'-[3-methylphenyl]urea (prepared from t-butyl 1-piperazinecarboxylate and 1-propyl-1,2,3,4-tetrahydro-3H-1,4-benzodiazepin-2,5-dione; Example 9, Step A) as described in Example 9, Step B. mp 131°–134° C. MS, CI$^+$, m/z=435 for (M+H)$^+$. Rf 0.11 in dichloromethane/methanol (9:1) on silica plates. Found: C, 64.32; H, 7.21; N, 18.71. $C_{24}H_{30}N_6O_2 \cdot 0.75H_2O$ requires C, 64.34; H, 7.09; N, 18.76%.

EXAMPLE 37

N-[3(R,S)-2,3-Dihydro-5-(4-ethylpiperazin-1-yl)-2-oxo-1-propyl-1H-1,4-benzodiazepin-3-yl]-N'-[3-methylphenyl]urea To a stirred solution of N-[3(R,S)-2,3-dihydro-2-oxo-5-(piperazin-1-yl)-1-propyl-1H-1,4-benzodiazepin-3-yl]-N'-[3-methylphenyl]urea (94 mg) in methanol (10 ml) was added sodium cyanoborohydride (27 mg), glacial acetic acid (54 μl) and acetaldehyde (36 μl). After stirring at room temperature for 45 minutes the solvent was evaporated and the residue partitioned between dichloromethane and saturated aqueous sodium hydrogen carbonate. The organic layer was separated and the aqueous further extracted with dichloromethane. The combined organics were dried (sodium sulphate) then evaporated to dryness to give the crude product which was recrystallised from ethyl acetate/ n-hexane (80 mg). mp 165°–168° C. Rf 0.43 in dichloromethane/methanol (9:1) on silica plates. $^1$H NMR (360 MHz, CDCl$_3$) δ0.77 (3H, t, J=7 Hz), 1.14 (3H, t, J=7 Hz), 1.26–1.60 (2H, m), 2.29 (3H, s), 2.40–2.76 (6H, m), 3.12–3.46 (4H, m), 3.50–3.60 (1H, m), 4.50–4.63 (1H, m), 5.24 (1H, d, J=7 Hz), 6.52 (1H, d, J=7 Hz), 6.78–7.60 (9H, m). Found: C, 66.06; H, 7.50; N, 17.95. $C_{26}H_{34}N_6O_2.0.5H_2O$ requires C, 66.22; H, 7.48; N, 17.82%.

EXAMPLE 38

N-[3(R,S)-2,3-Dihydro-7-methyl-5-(4-methylpiperazin-1-yl)-2-oxo-1-propyl-1H-1,4-benzodiazepin-3-yl]-N'-[3-methylphenyl]urea The title compound was obtained from methyl 5-methylanthranilate (mp 62° C. (water), prepared from 5-methylanthranilic acid) using the procedures described in Examples 8 and 33. mp 127°–130° C. MS, m/z=462 for M$^+$. $^1$H NMR (360 MHz, DMSO-d$_6$) δ0.68 (3H, t, J=7 Hz), 1.14–1.40 (2H, m), 2.19 (3H, s), 2.22 (3H, s), 2.24–2.48 (7H, m), 3.04–3.24 (4H, m), 3.58–3.62 (1H, m), 4.20–4.25 (1H, m), 4.92 (H, d, J=8 Hz), 6.70 (1H, d, J=8 Hz), 7.02 (1H, d, J=8 Hz), 7.04–7.12 (2H, m), 7.16 (1H, s), 7.33 (1H, d, J=2 Hz), 7.46 (1H, dd, J$_1$=2, J$_2$=8 Hz), 7.54 (1H, d, J=8 Hz), 8.80 (1H, s). Found: C, 65.74; H, 7.31; N, 17.64. $C_{26}H_{34}N_6O_2.0.7H_2O$ requires C, 65.72; H, 7.51; N, 17.69%.

EXAMPLE 39

N-[3(R,S)-2,3-Dihydro-5-(4-methylpiperazin-1-yl)-2-oxo-1-propyl-1H-1,4-benzodiazepin-3-yl]-N'-[3-(acetylamino)phenyl]urea The title compound was obtained from 3-amino-1,2-dihydro-5-(4-methylpiperzin-1-yl)-1-propyl-3H-1,4-benzodiazepin-2-one (obtained from the trifluoroacetate salt), m-acetamidoaniline and triphosgene. mp 172°–174° C. Found: C, 62.25; H, 6.71; N, 19.31. $C_{26}H_{33}N_7O_3.0.5H_2O$ requires C, 62.38; H, 6.85; N, 19.59%.

EXAMPLE 40

(+)-N-[2,3-Dihydro-5-(4-methylpiperazin-1-yl)-2-oxo-1-propyl-1H-1,4-benzodiazepin-3-yl]-N'-[3-(methylaminocarbonylamino)phenyl]urea The title compound was obtained from enantiomerically pure 3-amino-1,2-dihydro-5-(4-methylpiperazin-1-yl)-1-propyl-3H-1,4-benzodiazepin-2-one trifluoroacetate (Example 34), m-(methylaminocarbonylamino)aniline (prepared from m-nitroaniline) and triphosgene as described in Example 34. mp 193°–196° C. [α]$_D$=+43° (c=0.2, methanol). Found: C, 60.59; H, 6.69; N, 20.80. $C_{26}H_{34}N_8O_3.0.4H_2O.0.4\ C_4H_8O_2$ requires C, 60.38; H, 6.98; N, 20.41%.

EXAMPLE 41

(−)-N-[2,3-Dihydro-5-(4-methylpiperazin-1-yl)-2-oxo-1-propyl-1H-1,4-benzodiazepin-3-yl]-N'-[3-(dimethylamino)phenyl]urea The title compound was obtained from enantiomerically pure 3-amino-1,2-dihydro-5-(4-methylpiperazin-1-yl)-1-propyl-3H-1,4-benzodiazepin-2-one trifluoroacetate (Example 34), m-(dimethylamino)aniline and triphosgene as described in Example 34. mp 134°–136° C. [α]$_D$=−73° (c=0.1, methanol). Found: C, 64.28; H, 7.17; N, 20.06. $C_{26}H_{35}N_7O_2.0.5H_2O$ requires C, 64.17; H, 7.46; N, 20.15%.

EXAMPLE 42

N-[3(R,S)-2,3-Dihydro-8-methyl-5-(4-methylpiperazin-1-yl)-2-oxo-1-propyl-1H-1,4-benzodiazepin-3-yl]-N'-[3-methylphenyl]urea The title compound was obtained from methyl 4-methylanthranilate (J. Med. Chem., 1968, 11, 500) using the procedures described in Examples 8 and 33. mp 189°–191° C. MS, m/z=463 for (M+H)$^+$. $^1$H NMR (360 MHz, DMSO-d$_6$) δ0.67 (3H, t, J=7 Hz), 1.16–1.36 (2H, m), 1.38–1.47 (2H, m), 2.16 (3H, s), 2.21 (3H, s), 2.25–2.33 (2H, m), 2.38 (3H, s), 3.13 (4H, broad s), 3.59–3.67 (1H, m), 4.19–4.27 (1H, m), 4.92 (1H, d, J=8 Hz), 6.70 (1H, d, J=7 Hz), 6.99–7.21 (5H, m), 7.40 (1H, d, J=8 Hz), 7.47 (1H, s), 8.80 (1H, s).

EXAMPLE 43

N-[3(R,S)-2,3-Dihydro-5-(heptamethyleneimin-1-yl)-1-methyl-2-oxo-1H -1,4-benzodiazepin-3-yl]-N'-[3-methylphenol]urea Step A: 1,3-Dihydro-2H-5-(heptamethyleneimin-1-yl)-1-methyl-1,4-benzodiazepin-2-one A solution of phosphorus pentachloride (6.74 g) in dichloromethane (360 ml) was added dropwise to a stirred suspension of 1-methyl-1,2,3,4-tetrahydro-3H-1,4-benzodiazepin-2,5-dione (Example 1, 5.0 g). After stirring for 3 hours at room temperature the solvent was evaporated and the resulting foam re-dissolved in fresh dichloromethane (200 ml), cooled to 4° C. (ice bath) and a solution of heptamethyleneimine (10 g) in dichloromethane (100 ml) was added dropwise. The cooling bath was removed And the solution was stirred at room temperature for 16 hours. The reaction mixture was washed with saturated potassium hydrogen carbonate solution (300 ml), dried (sodium sulphate) then evaporated to give a gum (9.95 g). This gum was purified by column chromatography on silica using dichloromethane/methanol/ammonia (50:1:0.5 to 20:1:0.5), gradient elution. The required product was obtained as a glassy solid (5.90 g) from diethyl ether. mp>60° C. Rf 0.30 in dichloromethane/methanol (9:1) on silica plates. $^1$H NMR (360 MHz, CDCl$_3$) δ1.42–1.80 (10H, m), 3.34 (3H, s), 3.51 (1H, d, J=12 Hz) overlapped with 3.40–3.60 (4H, m), 4.25 (1H, d, J=12 Hz), 7.22–7.52 (4H, m). Found: C, 71.91; H, 7.68; N, 15.00. $C_{17}H_{23}N_3O$ requires C, 71.54; H, 8.12; N, 14.72%.

Step B: 1,3-Dihydro-2H-5-(heptamethyleneimin-1-yl)-1-methyl-3-oximido-1,4-benzodiazepin-2-one Potassium t-butoxide (4.28 g) was added in portions to a stirred, cooled (−20° C.) suspension of the foregoing benzodiazepine (4.0 g) in Anhydrous toluene (100 ml), under a nitrogen atmosphere. After stirring at −20° C. for 20 minutes isopentylnitrite (2.25 ml) was added dropwise and the reaction mixture was stirred at −20° C. for 2 hours. The mixture was treated with ethyl acetate (80 ml) and water (80 ml) containing citric acid (2.94 g). The reaction mixture was stirred whilst warming to room temperature then basified to pH=7 with potassium carbonate. The organic layer was separated and the aqueous re-extracted with ethyl acetate (3×80 ml). The combined organics were dried (sodium sulphate) then evaporated to give a semi-solid which was crystallised from ethyl acetate/diethyl ether (1:1) to afford the oxime as a beige solid (2.30 g). mp 176°–178° C. Rf 0.56/0.52 (E/Z isomers) in dichloromethane/methanol (9:1) on silica plates. MS. CI$^+$, m/z=315 for (M+H)$^+$. Found: C, 64.63; H, 6.98; N, 17.31. $C_{17}H_{22}N_4O_2$ requires C, 64.95; H, 7.05; N, 17.82%.

Step C: 3(R,S)-Amino-1,3-dihydro-2H-5-(heptamethyleneimin-1-yl)-1-methyl-1,4-benzodiazepin-2-one The foregoing oxime (0.50 g) was hydrogenated over 5% rhodium on carbon (0.50 g) in methanol (50 ml) at 40 psi and 60° C. for 5 hours. The reaction mixture was filtered, then evaporated to dryness to afford the title amine (0.47 g) as a beige gum, which was used immediately in the next step.

Step D: N-[3(R,S)-2,3-Dihydro-5-(heptamethyleneimin-1-yl)-1-methyl-2-oxo-1H-1,4-benzodiazepin-3-yl]-N'-[3-methylphenyl]urea m-Tolylisocyanate (0.20 ml) was added to a cooled (4° C.) solution of 3(R,S)-amino-1,3-dihydro-2H-5-(heptamethyleneimin-1-yl)-1-methyl-1,4-benzodiazepin-2-one (0.47 g, 1.56 mmol) in anhydrous tetrahydrofuran (8 ml). After standing at 4° C. for 1 hour the solution was evaporated to dryness and the residue re-dissolved in ethyl acetate (30 ml) then washed with water (10 ml). The organic layer was dried (sodium sulphate) then evaporated to give a yellow gum which was purified by column chromatography on silica using dichloromethane/methanol (50:1 to 25:1), gradient. The title compound was obtained as a colourless solid (180 mg). mp 193°–194° C. (dichloromethane/diethyl ether (1:1)). Rf 0.68 in dichloromethane/methanol (9:1) on silica plates. MS, CI$^+$, m/z=434 for (M+H)$^+$. $^1$H NMR (360 MHz, CDCl$_3$) δ1.45–1.90 (10H, m), 2.29 (3H, s), 3.40 (3H, s) overlapped with 3.30–3.65 (4H, m), 5.24 (1H, d, J=8 Hz), 6.30 (1H, d, J=8 Hz), 6.81–7.51 (9H, m). Found: C, 62.73; H, 6.30; N, 14.53. $C_{25}H_{31}N_5O_2.0.7CH_2Cl_2$ requires C, 62.61; H, 6.62; N, 14.21%.

EXAMPLE 44

N-[3(R,S)-2,3-Dihydro-2-oxo-5-(piperidin-1-yl)-1-propyl-1H-1,4-benzodiazepin-3-yl]-N'-[3-methylphenyl]urea Step A: 1,3-Dihydro-2H-5-(piperidin-1-yl)-1-propyl-1,4-benzodiazepin-2-one The title compound was obtained from 1-propyl-1,2,3,4-tetrahydro-3H-1,4-benzodiazepin-2,5-dione (Example 8) and piperidine as described in Example 43. The hydrochloride salt had mp 264°–268° C. Found: C, 62.76; H, 7.39; N, 12.86. $C_{17}H_{23}N_3O.HCl.0.25H_2O$ requires C, 62.57; H, 7.57; N, 12.87%.

Step B: N-[3(R,S)-2,3Dihydro-2-oxo-5-(piperidin-1-yl)-1-propyl-1H-1,4-benzodiazepin-3-yl]-N'-[3-methylphenyl]urea The title compound was obtained from 1,3-dihydro-2H-5-(piperidin-1-yl)-1-propyl-1,4-benzodiazepin-2-one as described in Example 43. The hydrochloride salt had mp 227° C. (dichloromethane/diethyl ether). Rf 0.70 in dichloromethane/methanol (9:1) on silica plates. $^1$H NMR (360 MHz, CDCl$_3$) δ0.79 (3H, t, J=7 Hz), 1.36–1.80 (8H, m), 2.30 (3H, s), 3.10–3.40 (4H, m), 3.50–3.60 (1H, m), 4.30–4.40 (1H, m), 5.23 (1H, d, J=8 Hz), 6.40 (1H, d, J=8 Hz), 6.60 (1H, broad s), 6.80–7.60 (8H, m). Found: C, 65.01; H, 7.07; N, 15.05. $C_{25}H_{31}N_5O_2.0.75HCl$ requires C, 65.15; H, 6.94; N, 15.19%.

EXAMPLE 45

N-[3(R,S)-2,3-Dihydro-8-dimethylamino-5-(4-methylpiperazin-1-yl)-2-oxo-1-propyl-1H-1,4-benzodiazepin-3-yl]-N'-[3-methylphenyl]urea Step A: Methyl 4-nitro-N-propyl-anthranilate To a stirred suspension of methyl 4-nitroanthranilate (prepared from 4-nitroanthranilic acid, 14.2 g) in methanol (600 ml) was added propionaldehyde (5.04 g) followed by glacial acetic acid (7.2 ml). Sodium cyanoborohydride (4.56 g) was added and the reaction mixture stirred at room temperature for 16 hours. Further propionaldehyde (5.04 g) and sodium cyanoborohydride (4.56 g) were added and the mixture stirred for a further 24 hours. The solvent was evaporated and the residue partitioned between ethyl acetate and 10% potassium carbonate solution. The organic layer was separated and the aqueous re-extracted with ethyl acetate (2×100 ml). The combined organics were washed with saturated sodium chloride solution then dried (sodium sulphate) and evaporated to give the crude product, which was purified by column chromatography on silica using 10% diethyl ether/petroleum ether (60–80) to afford the required product (3.42 g, 20%). $^1$H NMR (250 MHz, DMSO-d$_6$) δ0.98 (3H, t), 1.66 (2H, sextet), 3.26 (2H, dq), 3.86 (3H, s), 7.33 (1H, dd), 7.46 (1H, d), 7.88 (1H, t), 8.04 (1H, d).

Step B: 1,3-Dihydro-2H-5-(4-methylpiperazin-1-yl)-8-nitro-1-propyl-1,4-benzodiazepin-2-one The title compound was obtained from the foregoing anthranilate as described in Example 8. $^1$H NMR (250 MHz, DMSO-d$_6$) δ0.68 (3H, t), 1.14–1.54 (2H, m), 2.22 (3H, s), 2.24–2.56 (4H, m), 3.06–3.40 (4H, m), 3.44 (1H, d), 3.68 (1H, m), 4.04 (1H, d), 4.26 (1H, m), 7.74 (1H, d), 8.10 (1H, dd), 8.34 (1H, d).

Step C: 1,3-Dihydro-8-dimethylamino-2H-5-(4-methylpiperazin-1-yl)-1-propyl-1,4-benzodiazepin-2-one The foregoing benzodiazepine (2.64 g) was hydrogenated at 50 psi over 5% palladium on carbon (100 mg) in methanol (50 ml) for 3 hours. The reaction mixture was faltered then evaporated to dryness to give the crude amine which was purified by column chromatography on silica using 0.5% ammonia/5% methanol in dichloromethane to obtain 8-amino-1,3-dihydro-2H-5-(4-methylpiperazin-1-yl)-1-propyl-1,4-benzodiazepin-2-one (2.10 g). Sodium cyanoborohydride (1.68 g) was added to a stirred suspension of the amine (1.68 g) and paraformaldehyde (1.60 g, 53 mmol) in glacial acetic acid (50 ml). The reaction mixture was stirred at room temperature for 2 days then treated with 25% sodium hydroxide solution to pH=11 and extracted with dichloromethane (3×50 ml). The combined organics were dried (sodium sulphate) then evaporated to give the title compound as a foam (1.64 g). $^1$H NMR (250 MHz, DMSO-d$_6$) δ0.68 (3H, t), 1.16–1.50 (2H, m), 2.16 (3H, s), 2.20–2.48 (4H, m), 2.96 (6H, s), 3.04–3.20 (4H, m), 3.37 (1H, d), 3.46–3.64 (1H, m), 3.88 (1H, d), 4.10–4.28 (1H, m), 6.64 (2H, m), 7.26 (1H, d).

Step D: N-[3(R,S)-2,3-Dihydro-8-dimethylamino-5-(4-methylpiperazin-1-yl)-2-oxo-1-propyl-1H-1,4-benzodiazepin-3-yl]-N'-[3-methylphenyl]urea The title compound was obtained from the preceding benzodiazepine as described in Example 8. The hydrochloride salt had mp 214° C. MS, CI$^+$, m/z=492 for (M+H)$^+$. $^1$H NMR (360 MHz, D$_2$O) δ0.74 (3H, t, d=7 Hz), 1.42–1.68 (2H, m), 2.30 (3H, s), 3.03 (3H, s), 3.12 (6H, s), 3.30–4.10 (9H, m), 4.30 (1H, m), 5.56 (1H, s), 6.82 (1H, d, J=2 Hz), 6.90 (1H, dd, J$_1$=2, J$_2$=9 Hz), 7.04 (1H, d, J=9 Hz), 7.18 (2H, m), 7.28 (1H, dd, J$_1$=J$_2$=9 Hz), 7.52 (1H, d, d=9 Hz).

EXAMPLE 46

N-[3(R,S)-2,3-Dihydro-5-(homopiperidin-1-yl)-1-methyl-2-oxo-1H-1,4-benzodiazepin-3-yl]-N'-[5-indanyl]urea The title compound was obtained (145 mg) from 3-amino-1,2-dihydro-5-(homopiperidin-1-yl)-1-methyl-3H-1,4- benzodiazepin-2-one and 5-aminoindan as described in Example 14, Step B. mp>130° C. (dichloromethane). Rf 0.50 in dichloromethane/methanol (9:1) on silica plates. MS, Cl$^+$, m/z=446 for (M+H)$^+$. $^1$H NMR (360 MHz, CDCl$_3$) δ1.40–1.80 (8H, m), 1.99–2.08 (2H, m), 2.80–2.87 (4H, m), 3.34–3.46 (7H, m), 5.24 (1H, d, J=8 Hz), 6.33 (1H, d, J=8 Hz), 6.74 (1H, s), 7.01 (1H, dd, J$_1$=2 Hz, J$_2$=8 Hz), 7.09 (1H, d, J=8 Hz), 7.20–7.32 (3H, m), 7.45–7.51 (2H, m). Found: C, 63.37; H, 6.43; N, 13.93. C$_{26}$H$_{31}$N$_5$O$_2$.0.7CH$_2$Cl$_2$ requires C, 63.50; H, 6.47; N, 13.87%.

EXAMPLE 47

N-[3(R,S)-2,3-Dihydro-5-(homopiperidin-1-yl)-2-oxo-1-propyl-1H-1,4-benzodiazepin-3-yl]-N'-[3-methylphenyl]urea Step A: 1,2-Dihydro-5-(homopiperidin-1-yl)-1-propyl-3H-1,4-benzodiazepin-2one Carrying out Steps 1A–1D using homopiperidine and 1-propyl-1,2,3,4-tetrahydro-3H-1,4-benzodiazepin-2,5-dione afforded the title compound as a pale yellow solid (10.5 g). mp 115°–118° C. The hydrochloride salt had mp 186°–188° C. (Ethyl Acetate). MS, Cl$^+$, m/z=300 for (M+H)$^+$ of free base. Found: C, 60.90; H, 7.79; N, 11.79. C$_{18}$H$_{25}$N$_3$O.HCl.H$_2$O requires C, 61.09; H, 7.97; N, 11.87%.

Step B: 1,2-Dihydro-5-(homopiperidin-1-yl)-3-oximido-1-propyl-3H-1,4-benzodiazepin-2-one Carrying out Step 1E using the foregoing benzodiazepine and leaving the reaction mixture at −20° C. for 6 hours afforded the title compound as a cream solid (2.40 g). mp 163°–165° C. (Ethyl acetate/n-hexane). MS, Cl$^+$, m/z=329 for (M+H)$^+$. Found: C, 65.66; H, 7.32; N, 16.87. C$_{18}$H$_{24}$N$_4$O$_2$ requires C, 65.83; H, 7.37; N, 17.06%.

Step C: N-(3(R,S)-2,3-Dihydro-5-(homopiperidin-1-yl)-2-oxo-1-propyl-1H-1,4-benzodiazepin-3-yl]-N'-[3-methylphenyl]urea The title compound was obtained from the foregoing oxime as described in Example 19. mp 190°–192° C. (ethyl acetate). Found: C, 69.57; H, 7.37; N, 15.53. C$_{26}$H$_{33}$N$_5$O$_2$ requires C, 69.77; H, 7.43; N, 15.65%.

EXAMPLE 48

N-[3(R,S)-2,3-Dihydro-5-(homopiperidin-1-yl)-1-methyl-2-oxo-1H-1,4-benzodiazepin-3-yl]-N'-[3-trifluoromethylphenyl]urea The title compound was obtained from 3-amino-1,2-dihydro-5-(homopiperidin-1-yl)-1-methyl-3H-1,4-benzodiazepin-2-one (Example 20) and 3-trifluoromethylphenyl isocyanate as described in Example 19. mp 127°–130° C. (dichloromethane/diethyl ether). R$_f$ 0.70 in dichloromethane/methanol (9:1) on silica plates. MS, Cl$^+$, m/z 474 for (M+H)$^+$. Found: C, 59.79; H, 5.48; N, 14.45. C$_{24}$H$_{26}$F$_3$N$_5$O$_2$.0.5H$_2$O requires C, 59.74; H, 5.64; N, 14.51%.

EXAMPLE 49

N-[3(R,S)-2,3-Dihydro-5-(homopiperidin-1-yl)-1-methyl-2-oxo-1H-1,4-benzodiazepin-3-yl]-N'-[3-(dimethylamino)phenyl]urea The title compound was obtained from 3-amino-1,2-dihydro-5-(homopiperidin-1-yl)-1-methyl-3H-1,4-benzodiazepin-2-one (Example 20), m-(dimethylamino)aniline and triphosgene. mp 246°–247° C. Found: C, 66.30; H, 7.17; N, 18.41. C$_{25}$H$_{32}$N$_6$O$_2$.0.1H$_2$O requires C, 66.67; H, 7.21; N, 18.66%.

EXAMPLE 50

N-[3(R,S)-2,3-Dihydro-5-(homopiperidin-1-yl)-1-methyl-2-oxo-1H-1,4-benzodiazepin-3-yl]-N'-[4-t-butylphenyl]

The title compound was obtained from 3-amino-1,2-dihydro-5-(homopiperidin-1-yl)-1-methyl-3H-1,4-benzodiazepin-2-one (Example 20), 4-t-butylaniline and triphosgene. mp 239°–241° C. Found: C, 68.77; H, 7.64; N, 14.94. C$_{27}$H$_{35}$N$_5$O$_2$.0.5H$_2$O requires C, 68.90; H, 7.71; N, 14.88%.

EXAMPLE 51

(−)-N-[2,3-Dihydro-5-(heptamethyleneimin-1-yl)-1-methyl-2-oxo-1H-1,4-benzodiazepin-3-yl]-N'-[3-methylphenyl]urea hydrochloride N-[3(R,S)-2,3-Dihydro-5-(heptamethyleneimin-1-yl)-1-methyl-2-oxo-1H-1,4-benzodiazepin-3-yl]-N'-[3-methylphenyl]urea (Example 43, 150 mg) was separated into its two enantiomers using a semi-preparative dinitrobenzoylleucine Pirkle column (5μ) [(250×20)mm] eluting with 5% methanol in 1-chlorobutane (including 1% acetic acid).

The free base was liberated and obtained as a colourless solid (48 mg). The hydrochloride salt had mp 182° C.–184° C. (acetone/ethyl acetate (1:3)). Rf 0.68 in dichloromethane/methanol (9:1) on silica plates. [α]$^{23°}$ $^C{}_D$=−83° (c=0.2, methanol). Found: C, 61.92; H, 6.92; N, 14.30. C$_{25}$H$_{31}$N$_5$O$_2$.HCl.0.75H$_2$O requires C, 62.10; H, 6.98; N, 14.48%.

EXAMPLE 52

(+)-N-[2,3-Dihydro-5-(heptamethyleneimin-1-yl)-1-methyl-2-oxo-1H-1,4-benzodiazepin-3-yl]-N'-[3-methylphenyl]urea hydrochloride The title compound was obtained (38 mg) using the procedure described in Example 51. mp 179° C.–181° C. (acetone/ethyl acetate (1:3)). Rf 0.68 in dichloromethane/methanol (9:1) on silica plates. [α]23° C.$_D$=+80.5° (c=0.2, methanol). Found: C, 62.17; H, 7.19; N, 14.34. C$_{25}$H$_{31}$N$_5$O$_2$.HCl.0.75H$_2$O requires C, 62.10; H, 6.98; N, 14.48%.

EXAMPLE 53

N-[3(R,S)-2,3-Dihydro-5-(4-methylpiperazin-1-yl)-2-oxo-1-propyl-1H-1,4-benzodiazepin-3-yl]-N'-[4-(dimethylamino)phenyl]urea The title compound was obtained from 3-amino-1,2-dihydro-5-(4-methylpiperazin-1-yl)-1-propyl-3H-1,4-benzodiazepin-2-one, 4-(dimethylamino)aniline and triphosgene. mp 226° C.–228° C. Found: C, 65.57; H, 7.29; N, 20.62. C$_{26}$H$_{35}$N$_7$O$_2$ requires C, 65.39; H, 7.40; N, 20.53%.

EXAMPLE 54

N-[3(R,S)-2,3-Dihydro-5-(homopiperidin-1-yl)-1-methyl-2-oxo-1H-1,4-benzodiazepin-3-yl]-N'-[4-isopropylphenyl]urea The title compound was obtained from 3-amino-1,2-dihydro-5-(homopiperidin-1-yl)-1-methyl-3H-1,4- benzodiazepin-2-one (Example 20), 4-isopropylaniline and triphosgene. mp 240°–242° C. (methanol). Rf 0.57 in 10% methanol/dichloromethane on silica plates. MS, CI$^+$, m/z=448 for (M+H)$^+$. Found: C, 69.53; H, 7.35; N, 15.61. $C_{26}H_{33}N_5O_2$ requires C, 69.77; H, 7.43; N, 15.65%.

EXAMPLE 55

N-[3(R,S)-2,3-Dihydro-2-oxo-1-propyl-5-(thiomorpholin-4-yl)-1H-1,4-benzodiazepin-3-yl]-N'-[3-methylphenyl]urea The title compound was obtained from 3-amino-1,2-dihydro- 1-propyl-5-(thiomorpholin-4-yl)-3H-1,4-benzodiazepin-2-one (prepared using the procedure described in Example 33) and m-tolylisocyanate. mp 240° C. Found: C, 64.09; H, 6.53; N, 15.54. $C_{24}H_{29}N_5O_2S$ requires C, 63.83; H, 6.47; N, 15.51%.

EXAMPLE 56

N-[3(R,S)-2,3-Dihydro-5-(4-methylpiperazin-1-yl)-2-oxo-1-propyl-1H-1,4-benzodiazepin-3-yl]-N'-[1-methyl-6-indolinyl]urea Step A: 1-Methyl-6-nitroindoline Potassium bis(trimethylsilyl)amide (67 ml of a 0.5M toluene solution) was added slowly to a stirred solution of 6-nitroindoline (5.0 g) in anhydrous tetrahydrofuran (200 ml) at −78° C. under a nitrogen atmosphere. Iodomethane (2.09 ml) was added then the reaction mixture was allowed to warm to room temperature then stirred overnight. Methanol (5 ml) was added then the solution was evaporated to dryness. The residue was dissolved in diethyl ether (300 ml), washed with water, saturated brine then dried (magnesium sulphate) and evaporated to dryness. The crude product was purified by column chromatography on silica using 10% ethyl acetate/petroleum ether (60–80)→30% ethyl acetate/petroleum ether (60–80) and the product crystallised from diethyl ether/petroleum ether (60–80) to afford 0.9 g.

Step B: 6-Amino-1-methylindoline

1-Methyl-6-nitroindoline (0.9 g) was hydrogenated at 40 psi in methanol (100 ml) containing 10% palladium on carbon (0.9 g). The reaction mixture was filtered then evaporated and the residue was purified by column chromatography on silica using hexane→50% ethyl acetate/hexane to afford the title compound (0.62 g).

Step C: N-[3(R,S)-2,3-Dihydro-5-(4-methylpiperazin-1-yl)-2-oxo-1-propyl-1H-1,4-benzodiazepin-3-yl]-N'-[1-methyl-6-indolinyl]urea The title compound was obtained from 3-amino-1,2-dihydro-5-(4-methylpiperazin-1-yl)-1-propyl -3H-1,4-benzodiazepin-2-one, 6-amino-1-methylindoline and triphosgene. mp 225° C. Found: C, 66.00; H, 7.03; N, 19.66. $C_{27}H_{35}N_7O_2$ requires C, 66.23; H, 7.21; N, 20.03%.

EXAMPLE 57

N-[3(R,S)-2,3-Dihydro-5-(homopiperidin-1-yl)-1-methyl-2-oxo-1H-1,4-benzodiazepin-3-yl]-N'-[3,4-difluorophenyl]urea Triphosgene (231 mg) and triethylamine (0.8 ml) were added to a stirred solution of 3-amino-1,2-dihydro-5-(homopiperidin-1-yl)-1-methyl-3H-1,4-benzodiazepin-2-one (Example 20, 0.6 g) in anhydrous tetrahydrofuran (8 ml) at 4° C. After stirring at 4° C. for 30 minutes 3,4-difluoroaniline (0.26 ml) was added. The cooling bath was removed and the reaction mixture was stirred at room temperature for 24 hours. The reaction mixture was evaporated to dryness then the residue partitioned between ethyl acetate and saturated sodium carbonate solution. The organic layer was separated, dried (sodium sulphate) then evaporated to give the crude product which was purified by column chromatography on silica using neat dichloromethane→1% methanol in dichloromethane→2% methanol in dichloromethane. The title compound was obtained (130 mg) as a solid. mp 230°–233° C. Rf 0.51 in 10% methanol in dichloromethane on silica plates. $^1$H NMR (360 MHz, CDCl$_3$) δ1.40–1.90 (8H, m), 3.40–3.66 (4H, m) overlapped with 3.43 (3H, s), 5.31 (1H, d, J=8 Hz), 6.64 (1H, broad d, J=8 Hz), 6.90–7.60 (7H, m), 7.95 (1H, broad s). Found: C, 61.62; H, 5.64; N, 15.14. $C_{23}H_{25}F_2N_5O_2 \cdot 0.5H_2O$ requires C, 61.32; H, 5.82; N, 15.54%.

EXAMPLE 58

(−)-N-[2,3-Dihydro-5-(homopiperidin-1-yl)-1-methyl-2-oxo-1H-1,4-benzodiazepin-3-yl]-N'-[5-indanyl]urea hydrochloride N-[3(R,S)-2,3-Dihydro-5-(homopiperidin-1-yl)-1-methyl-2-oxo-1H-1,4-benzodiazepin-3-yl]-N'-[5-indanyl]urea (Example 46, 2.6 g) was separated into its two enantiomers using a semi-preparative dinitrobenzoylleucine Pirkle column (5μ) [(250×20)mm] eluting with 3% methanol in 1-chlorobutane (including 1% acetic acid).

The free base was liberated and obtained as a colourless solid (840 mg). The hydrochloride salt had mp 195° C. (dec) (acetone/ethyl acetate (1:1)). Rf 0.62 in 10% methanol in dichloromethane on silica plates. [α]$^{23°}$ $^C_D$=−162.5° (c=0.2, methanol). Found: C, 62.87; H, 6.78; N, 14.00. $C_{26}H_{31}N_5O_2 \cdot HCl \cdot 0.75H_2O$ requires C, 63.02; H, 6.81; N, 14.13%.

EXAMPLE 59

(+)-N-(2,3-Dihydro-5-(homopiperidin-1-yl)-1-methyl-2-oxo-1H-1,4-benzodiazepin-3-yl]-N'-[5-indanyl]urea hydrochloride The title compound free base was obtained (900 mg) using the procedure described in Example 58. The hydrochloride salt had mp 195° C. (dec). Rf 0.62 in 10% methanol in dichloromethane on silica plates. [α]$^{23°}$ $^C_D$=+159° (c=0.2, methanol). Found: C, 62.81; H, 6.86; N, 14.08. $C_{26}H_{31}N_5O_2 \cdot HCl \cdot 0.75H_2O$ requires C, 63.02; H, 6.81; N, 14.13%.

EXAMPLE 60

N-[3(R,S)-2,3-Dihydro-5-(homopiperidin-1-yl)-1-methyl-2-oxo-1H-1,4-benzodiazepin-3-yl]-N'-[3-fluorophenyl]urea The title compound was obtained (178 mg) from 3(R,S)-amino-1,2-dihydro-3H-5-(homopiperidin-1-yl)-1-methyl-1,4-benzodiazepin-2-one (Example 20, Step B) and 3-fluorophenylisocyanate as described in Example 19. mp 216°–218° C. (ethyl acetate/diethyl ether). Rf 0.61 in dichloromethane/methanol (9:1) on silica plates. MS, CI$^+$, m/z=424 for (M+H)$^+$. Found: C, 65.22; H, 6.25; N, 16.12. $C_{23}H_{26}FN_5O_2$ requires C, 65.23; H, 6.19; N, 16.54%.

EXAMPLE 61

N-[3(R,S)-2,3-Dihydro-1-methyl-5-(octamethyleneimin-1-yl)-2-oxo-1H-1,4-benzodiazepin-3-yl ]-N'-[3-methylphenyl]urea Step A: Octamethyleneimine A 1M solution of borane-tetrahydrofuran in tetrahydrofuran (284 ml) was added dropwise to a stirred, cooled (4° C.) solution of 2-azacyclononanone (20 g) in anhydrous tetrahydrofuran (150 ml) under a nitrogen atmosphere. After addition the reaction mixture was heated at reflux for 1 hour then stirred at room temperature for 5 hours. A saturated solution of potassium carbonate (19.6 g) in water was added cautiously then the mixture was heated at reflux for 30 minutes. The tetrahydrofuran was evaporated and the residue treated with 5M hydrochloric acid (100 ml). The mixture was stirred at room temperature for 1 hour then washed with dichloromethane (100 ml). The aqueous was basified to pH=12 using 40% aqueous sodium hydroxide then extracted with dichloromethane (3×100 ml). The combined organics were dried (potassium carbonate) then evaporated to dryness to give a pale yellow oil which was purified by vacuum distillation (10.5 g), bp 120°–124° C. (120 mmHg), Rf 0.10 in dichloromethane/methanol (9:1) on silica plates.

Step B: N-[3(R,S)-2,3-Dihydro-1-methyl-5-(octamethyleneimin-1-yl)-2-oxo-1H-1,4-benzodiazepin-3-yl]-N'-[3-methylphenyl]urea The title compound was obtained from octamethyleneimine and 1-methyl-1,2,3,4-tetrahydro-3H-1,4-benzodiazepin-2,5-dione using the procedures described in Example 43. mp 131°–132° C. (dichloromethane/diethyl ether). Rf 0.70 in dichloromethane/methanol (9:1) on silica plates. MS, CI$^+$, m/z=448 for (M+H)$^+$. Found: C, 69.41; H, 7.25; N, 15.47. $C_{26}H_{33}N_5O_2$ requires C, 69.77; H, 7.43; N, 15.65%.

EXAMPLE 62

N-[3(R,S)-2,3-Dihydro-5-(homopiperidin-1-yl)-1-methyl-2-oxo-1H-1,4-benzodiazepin-3-yl]-N'-[3-(5-hydroxy-4-pyron-2-yl)phenyl]urea Step A: 3-Acetoxy-6-(3-nitrophenyl)-4-pyrone n-Butyllithium (31.9 ml of a 1M hexane solution) was added dropwise to a stirred, cooled (−78° C.) solution of hexamethyldisilazane (10.8 ml) in anhydrous tetrahydrofuran (140 ml). After 20 minutes a solution of 2-acetoxy-1-methoxy-buten-3-one (8.0 g, Chem. Ber. 1959, 92, 3009–3015) in anhydrous tetrahydrofuran (60 ml) was added dropwise keeping the reaction mixture below −70° C. After a further 20 minutes a solution of 3-nitrobenzoylchloride (4.82 g) in anhydrous tetrahydrofuran (40 ml) was added dropwise. After addition the cooling bath was removed and the mixture warmed to −15° C. over 30 minutes. The reaction mixture was quenched with 2M hydrochloric acid (50 ml) then the organic layer was separated and the aqueous re-extracted with diethyl ether (2×100 ml). The combined organics were washed with brine (200 ml) then dried (sodium sulphate) then evaporated to give a viscous orange gum (14.10 g). This gum was dissolved in toluene (100 ml) and treated with pyridinium p-toluene sulphonate (1 g) then the mixture was heated at reflux for 1 hour. The reaction mixture was evaporated and the residue dissolved in chloroform (300 ml), washed sequentially with 10% sodium hydrogen carbonate solution (2×100 ml), water (100 ml) then dried (sodium sulphate) and evaporated to give a brown semi-solid (6.30 g) which was purified by column chromatography on silica using ethyl acetate. The product obtained was recrystallised from hot ethyl acetate to give the title compound as a cream solid (2.0 g). mp 170°–171° C. Rf 0.24 in ethyl acetate/n-hexane (1:1) on silica plates. MS, CI$^+$, m/z=276 for (M+H)$^+$. $^1$H NMR (360 MHz, CDCl$_3$) δ2.37 (3H, s), 7.00 (1H, s), 7.73 (1H, dd, J$_1$=J$_2$=8 Hz), 8.05–8.08 (2H, m), 8.39 (1H, dd, J$_1$=1 Hz, J$_2$=8.66 (1H, dd, J$_1$=J$_2$=1 Hz). Found: C, 56.98; H, 3.54; N, 4.97. $C_{13}H_9NO_6$ requires C, 56.73; H, 3.30; N, 5.09%.

Step B: 3-Acetoxy-6-(3-aminophenyl)-4-pyrone

The foregoing nitro compound (1.80 g) was hydrogenated at 10 psi over 10% palladium on carbon (200 mg) in methanol (50 ml) for 1 hour. The reaction mixture was filtered then evaporated and the crude product recrystallised from ethyl acetate/n-hexane (2:1) to afford the title compound as a beige solid (1.20 g). mp 127°–129° C. Rf 0.46 in ethyl acetate on silica plates. MS, CI$^+$, m/z=246 for (M+H)$^+$. $^1$H NMR (360 MHz, CDCl$_3$) δ2.85 (3H, s), 3.85 (2H, broad resonance), 6.81 (1H, dd, J$_1$=1 Hz, J$_2$=8 Hz), 6.84 (1H, s), 7.02 (1H, dd, J$_1$=J$_2$=1 Hz), 7.11 (1H, broad d, J=8 Hz), 7.25 (1H, dd, J$_1$=J$_2$=8 Hz), 7.98 (1H, s). Found: C, 62.52; H, 4.90; N, 5.44. $Cl_3H_{11}NO_4.0.25H_2O$ requires C, 62.52; H, 4.64; N, 5.61%.

Step C: N-[3(R,S)-2,3-Dihydro-5-(homopiperidin-1-yl)-1-methyl-2-oxo-1H-1,4-benzodiazepin-3-yl]-N'-[3-(5-acetoxy-4-pyron-2-yl)phenyl]urea The title compound was obtained from 3-acetoxy-6-(3-aminophenyl)-4-pyrone, triphosgene and 3(R,S)-amino-1,2-dihydro-3H-5-(homopiperidin-1-yl)-1-methyl-1,4-benzodiazepin-2-one (Example 20, Step B) as described in Example 46. mp>150° C. (dec). $^1$H NMR (360 MHz, CDCl$_3$) δ1.45–1.85 (8H, m), 2.34 (3H, s), 3.47 (3H, s), 3.45–3.65 (4H, m), 5.42 (1H, d, J=8 Hz), 6.81 (1H, s), 7.24–7.41 (7H, m), 7.54–7.62 (2H , m), 7.92 (1H, s), 7.94 (1H, s).

Step D: N-[3(R,S)-2,3-Dihydro-5-(homopiperidin-1-yl)-1-methyl-2-oxo-1H-1,4-benzodiazepin-3-yl]-N'-[3-(5-hydroxy-4-pyron-2-yl)phenyl]urea Potassium carbonate (10 mg) was added to a stirred suspension of the foregoing acetate (27 mg) in methanol (6 ml) and the reaction mixture was stirred at room temperature for 1 hour. Citric acid (14 mg) was added then the solvent was evaporated. The residue was partitioned between water (5 ml) and dichloromethane (15 ml). The organic layer was separated and the aqueous re-extracted with dichloromethane (15 ml). The combined organics were dried (sodium sulphate) then evaporated to give a yellow solid which was recrystallised from hot ethyl acetate. mp>215° C. (dec). Rf 0.40 in dichloromethane/methanol (9:1) on silica plates. Found:C, 64.22; H, 5.99; N, 12.82. $C_{28}H_{29}N_5O_5.0.5H_2O$ requires C, 64.11; H, 5.76; N, 13.35%.

EXAMPLE 63

N-[3(R,S)-2,3-Dihydro-5-(homopiperidin-1-yl)-1-methyl-2-oxo-1H-1,4-benzodiazepin-3-yl]-N'-[3-ethylphenyl]urea The title compound was obtained (590 mg) from 3(R,S)-amino-1,2-dihydro-3H-5-(homopiperidin-1-yl)-1-methyl-1,4-benzodiazepin-2-one (Example 20, Step B) and 3-ethylphenyl isocyanate as described in Example 19. mp 213°–214° C. (ethyl acetate/diethyl ether). Rf 0.63 in dichloromethane/methanol (9:1) on silica plates. MS, CI$^+$, m/z=434 for (M+H)$^+$. Found: C, 69.45; H, 6.88; N, 16.01. $C_{25}H_{31}N_5O_2$ requires C, 69.26; H, 7.21; N, 16.15%.

EXAMPLE 64

N-[3(R,S)-2,3-Dihydro-1-ethyl-5-(homopiperidin-1-yl)-2-oxo-1H-1,4-benzodiazepin-3-yl]-N'-[3-methylphenyl]urea Step A: 1-Ethyl-1,2,3,4-tetrahydro-3H-1,4-benzodiazepin-2,5-dione Sodium hydride (28 g of a 55% oil dispersion) was added in portions to a stirred, cooled (4° C.) solution of isatoic anhydride (100 g) and iodoethane (104 g) in anhydrous dimethylformamide (600 ml). The reaction mixture was stirred at room temperature for 3 hours. The solvent was evaporated and the residue partitioned between ethyl acetate (1 l) and water (500 ml). The organic layer was separated, washed with brine (2×100 ml), dried (sodium sulphate) then evaporated to give a semi-solid which was triturated with diethyl ether to afford N-ethyl isatoic anhydride as a tan powder (70 g). N-Ethyl isatoic anhydride (64 g), glycine (27 g) and glacial acetic acid (500 ml) were heated at reflux for 4 hours. The solvent was evaporated and the residue was partitioned between dichloromethane (1.5 l) and saturated sodium hydrogen carbonate solution. The organic layer was separated, washed with 1M sodium hydroxide (200 ml), dried (magnesium sulphate), evaporated then the residue triturated with diethyl ether to afford the title compound as a beige solid (53 g). mp 169°–170° C. (ethyl acetate). Rf 0.50 in dichloromethane/methanol (9:1) on silica plates. $^1$H NMR (360 MHz, CDCl$_3$) δ1.21 (3H, t, J=7 Hz), 3.73–3.83 (3H, m), 4.13–4.22 (1H, m), 6.97 (1H, broad s), 7.26–7.36 (2H, m), 7.56 (1H, ddd, J$_1$=2 Hz, J$_2$=J$_3$=8 Hz), 7.89 (1H, dd, J$_1$=2 Hz, J$_2$=8 Hz). Found: C, 64.25; H, 5.92; N, 13.67. C$_{11}$H$_{12}$N$_2$O$_2$ requires C, 64.69; H, 5.92; N, 13.72%.

Step B: 1,2-Dihydro-1-ethyl-3H-5-(homopiperidin-1-yl)-1,4-benzodiazepin-2-one

The title compound was obtained (5.20 g) from 1-ethyl-1,2,3,4-tetrahydro-3H-1,4-benzodiazepin-2,5-dione, phosphorus pentachloride and homopiperidine as described in Example 43. mp 30°–35° C. (ethyl acetate/n-hexane). The hydrochloride salt had mp 195°–198° C. (ethyl acetate/ diethyl ether). Found: C, 58.97; H, 7.59; N, 12.07. C$_{17}$H$_{23}$N$_3$O.HCl.1.25H$_2$O requires C, 59.29; H, 7.76; N, 12.20%.

Step C: 1,2-Dihydro-1-ethyl-3H-5-(homopiperidin-1-yl)-3-oximido-1,4-benzodiazepin-2-one The title compound was obtained (1.87 g) from the foregoing benzodiazepine using the procedure described in Example 43. mp 175°–176° C. (ethyl acetate/diethyl ether). MS, CI$^+$, m/z=315 for (M+H)$^+$. Found: C, 64.99; H, 6.98; N, 17.59. C$_{17}$H$_{22}$N$_4$O$_2$ requires C, 64.95; H, 7.05; N, 17.82%.

Step D: N-[3(R,S)-2,3-Dihydro-1-ethyl-5-(homopiperidin-1-yl)-2-oxo-1H-1,4-benzodiazepin-3-yl]-N'-[3-methylphenyl]urea The title compound was obtained (275 mg) using the procedures described in Example 43, Steps C and D. mp 215°–217° C. (ethyl acetate/diethyl ether). Rf 0.65 in dichloromethane/methanol (9:1) on silica plates. $^1$H NMR (360 MHz, CDCl$_3$) δ1.14 (3H, t, J=7 Hz), 1.45–1.90 (8 H, m), 2.28 (3H, s), 3.40–3.60 (4H, m), 3.66–3.76 (1H, m), 4.28–4.38 (1H, m), 5.29 (1H, d, J=8 Hz), 6.68 (1H, broad d, J=8 Hz), 6.80–6.82 (1H, m), 7.11–7.56 (8H, m). Found: C, 65.50; H, 7.24; N, 14.01. C$_{25}$H$_{31}$N$_5$O$_2$.0.5CH$_3$CO$_2$CH$_2$CH$_3$.H$_2$O requires C, 65.43; H, 7.52; N, 14.13%.

EXAMPLE 65

N-[3(R,S)-2,3-Dihydro-1-methyl-2-oxo-5-(thiomorpholin-4-yl)-1H-1,4-benzodiazepin-3-yl]-N'-[3-methylphenyl]urea The title compound was obtained from 3-amino-1,2-dihydro-1-methyl-5-(thiomorpholin-4-yl)-3H-1,4-benzodiazepin-2-one (prepared using the procedure described in Example 33) and m-tolylisocyanate. mp 266°–268° C. Found: C, 61.92; H, 5.77; N, 16.15. C$_{22}$H$_{25}$N$_5$O$_2$S.0.15H$_2$O requires C, 61.99; H, 5.98; N, 16.43%.

EXAMPLE 66

N-[3(R,S)-2,3-Dihydro-5-(homopiperidin-1-yl)-1-methyl-2-oxo-1H-1,4-benzodiazepin-3-yl]-N'-phenyl urea The title compound was obtained from 3(R,S)-amino-1,2-dihydro-5-(homopiperidin-1-yl)-1-methyl-3H-1,4-benzodiazepin-2-one and phenyl isocyanate as described in Example 19. mp 218°–220° C. (dichloromethane/diethyl ether). Found: C, 66.55; H, 6.60; N, 16.93. C$_{23}$H$_{27}$N$_5$O$_2$.0.5H$_2$O requires C, 66.65; H, 6.81; N, 16.90%.

EXAMPLE 67

(−)-N-[2,3-Dihydro-5-(homopiperidin-1-yl)-1-methyl-2-oxo-1H-1,4-benzodiazepin-3-yl]-N'-[3-ethylphenyl]urea hydrochloride The racemate (470 mg, Example 63) was separated into its two enantiomers using a semi-preparative dinitrobenzoylleucine Pirkle column (5μ) [(250×20)mm] eluting with 5% methanol in 1-chlorobutane (including 1% acetic acid).

The free base was liberated and obtained as a colourless crystalline solid (180 mg). The hydrochloride salt had mp 190°–92° C. (acetone/ethyl acetate) (1:2). R$_f$ 0.63 in dichloromethane/methanol (9:1) on silica plates. [α]23° C.$_D$=−155° (c=0.2, methanol). $^1$H NMR (360 MHz, D$_2$O) δ1.17 (3H, t, J=8 Hz), 1.38–2.08 (8H, m), 2.60 (2H, q, J=8 Hz), 3.48 (3H, s), 3.62–3.74 (4H, m), 5.53 (1H, s), 7.05 (1H, d, J=8 Hz), 7.15 (1H, d, J=8 Hz), 7.22 (1H, s), 7.30 (1H, dd, J$_1$=J$_2$=8 Hz), 7.58 (1H, dd, J$_1$=J$_2$=8 Hz), 7.65 (1H, d, J=8 Hz), 7.78 (1H, d, J=8 Hz), 7.86 (1H, dd, J$_1$=J$_2$=8 Hz). Found: C, 61.55; H, 6.72; N, 14.36. C$_{25}$H$_{31}$N$_5$O$_2$.HCl.H$_2$O requires C, 61.53; H, 7.02; N, 14.35%.

EXAMPLE 68

(+)-N-[2,3-Dihydro-5-(homopiperidin-1-yl)-1-methyl-2-oxo-1H-1,4-benzodiazepin-3-yl]-N'-[3-ethylphenyl]urea hydrochloride The title compound free base was obtained (180 mg) using the procedure described in Example 67. The hydrochloride salt had mp 189°–190° C. (acetone/ethyl acetate) (1:2). Rf 0.63 in dichloromethane/methanol (9:1) on silica plates. [α]$^{23°}$ C.$_D$=+155° (c=0.2, methanol). Found: C, 62.96; H, 6.84; N, 15.07. C$_{25}$H$_{31}$N$_5$O$_2$.HCl.0.3H$_2$O requires C, 63.16; H, 6.91; N, 14.73%.

EXAMPLE 69

(−)-N-[2,3-Dihydro-2-oxo-1-propyl-5-(thiomorpholin-4-yl)-1H-1,4-benzodiazepin-3-yl]-N'-[3-methylphenyl]urea hydrochloride The title compound was obtained using the procedure described in Example 67. mp 201°–203° C. [α]$^{22°}$ C.$_D$=−177° (c=0.1, methanol). Found: C, 56.02; H, 6.26; N, 13.49. C$_{24}$H$_{29}$N$_5$O$_2$S.HCl.1.5H$_2$O requires C, 55.97; H, 6.46; N, 13.60%.

EXAMPLE 70

+-N-2,3Dihydro-2-oxo-1-propyl-5-thiomorpholin-4-yl)-1H-1,4-benzodiazepin-3-yl]-N'-[3-methylphenyl] urea hydrochloride The title compound was obtained using the procedure described in Example 67. mp 198°–200° C. [α]$^{22°}$ C.$_D$=+

112° (c=0.1, methanol). Found: C, 54.30; H, 6.27; N, 12.94. $C_{24}H_{29}N_5O_2S.HCl.2.5H_2O$ requires C, 54.07; H, 6.62; N, 13.14%.

EXAMPLE 71

N-[3(R,S)-2,3-Dihydro-5-(homopiperidin-1-yl)-1-methyl-2-oxo-1H-14-benzodiazepin-3-yl]-N'-3,4-methylenedioxy)phenyl]urea Step A: 1,2-Dihydro-5-(homopiperidin-1-yl)-1-methyl-3-(O-ethylaminocarbonyl)oximido)-3H-1,4-benzodiazepin-2-one 1,2-Dihydro-5-(homopiperidin-1-yl)-1-methyl-3-oximido-3H-1,4-benzodiazepin-2-one (Example 20), 426 mg) and ethyl isocyanate (0.17 ml) were heated at 60° C. in anhydrous tetrahydrofuran (20 ml) for 18 hours. The solvent was evaporated and the residue purified by column chromatography on silica using dichloromethane→1% methanol/dichloromethane to afford a cream foam (500 mg as a mixture of E/Z isomers.) mp 185° C. Rf 0.60 in dichloromethane/methanol (9:1) on silica plates. $^1$H NMR (360 MHz, CDCl$_3$) δ1.10 and 1.12 (3H, each t, J=7 Hz), 1.32–2.06 (8H, m), 3.14–3.30 (2H, m), 3.36–3.58 (3H, m) overlapped with 3.44 and 3.45 (3H, each s), 3.92–4.10 (1H, m), 6.13–6.22 and 6.34–6.46 (1H, each m), 7.18–7.52 (4H, m).

Step B: 3(R,S)-Amino-1,2-dihydro-5-(homopiperidin-1-yl)-1-methyl-3H-1,4-benzodiazepin-2-one The foregoing oxime derivative (140 mg) was hydrogenated at 45 psi in methanol (20 ml) over 10% palladium on carbon (50 mg) for 3 hours at room temperature. The mixture was filtered and the solvent evaporated to afford the amine as a beige foam (106 mg, 95%) which was used immediately in the next step.

Step C: N-[3(R,S)-2,3-Dihydro-5-(homopiperidin-1-yl)-1-methyl-2-oxo-1H-1,4-benzodiazepin-3-yl]-N'-3,4-methylenedioxy)phenyl]urea A cooled (4° C.), stirred, solution of 3,4-(methylenedioxy)aniline (56 mg) in anhydrous tetrahydrofuran (8 ml) was treated with triethylamine (0.1 ml) and triphosgene (40 mg). After stirring at 4° C. for 15 minutes a solution of 3(R,S)-amino-1,2-dihydro-5-(homopiperidin-1-yl)-1-methyl-3H-1,4-benzodiazepin-2-one (106 mg) in anhydrous tetrahydrofuran (7 ml) was added and the mixture stirred at 4° C. for 1 hour. The reaction mixture was evaporated to dryness and the residue partitioned between dichloromethane (25 ml) and water (10 ml). The organic layer was separated, washed with water (10 ml) then dried (sodium sulphate) and evaporated to give a cream semi-solid which was crystallised from dichloromethane to afford the title compound as a cream solid (108 mg). mp 234°–236° C. Rf 0.45 in dichloromethane/methanol (9:1) on silica plates. $^1$H NMR (360 MHz, CDCl$_3$) δ1.30–2.10 (8H, m), 3.43 (3H, s), 3.43–3.60 (4H, m), 5.34 (1H, d, J=8 Hz), 5.90 (2H, s), 6.67– 6.74 (3H, m), 7.04 (1H, d, J=2 Hz), 7.25–7.58 (5H, m).

EXAMPLE 72

N-[3(R,S)-2,3-Dihydro-5-(homopiperidin-1-yl)-1-methyl-2-oxo-1H-1,4-benzodiazepin-3-yl]-N'-[3-fluoro-4-methylphenyl]urea The title compound was obtained (344 mg) from 3(R,S)-amino-1,2-dihydro-5-(homopiperidin-1-yl)-1-methyl-3H-1,4-benzodiazepin-2-one, 3-fluoro-4-methylaniline and triphosgene. mp 232°–235° C. (dichloromethane). Rf 0.54 in dichloromethane/methanol (9:1) on silica plates. $^1$H NMR (360 MHz, CDCl$_3$) δ1.40–1.90 (8H, m), 2.17 (3H, d, J=1 Hz), 3.30–3.56 (4H, m) overlapped with 3.42 (3H, s), 5.27 (1H, d, J=8 Hz), 6.57 (1H, d, J=8 Hz), 6.98–7.58 (8H, m).

EXAMPLE 73A

Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 73B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 74

Parenteral injection

|  | Amount mg |
| --- | --- |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 75

Topical formulation

|  | Amount mg |
| --- | --- |
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM (HEPES)), 1 mM ethylene glycol-bis-($\beta$-eminoethylether-N,N'-tetraacetic acid) (EGTA), 5 mM MgCl$_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 µl of buffer (for total binding) or unlabelled CCK-8 sulphated to give a final concentration of 1 µM (for nonspecific binding) or the compounds of Formula I (for determination of inhibition of $^{125}$I-CCK-8 binding) and 50 µl of 500 pM $^{125}$I-CCK-8 (i.e. 50 pM final concentration) were added to 400 µl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32 M sucrose. The homogenates were centrifuged at 1000 g for 10 minutes and the resulting supernatant was recentrifuged at 20,000 g for 20 minutes. The P$_2$ pellet was resuspended in binding assay buffer (20 mM HEPES, 5 mM MgCl$_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 µl of buffer (for total binding) or Unlabelled CCK-8 sulphated to give a final concentration of 1 µM (for nonspecific binding) or the compounds of Formula I (for determination of inhibition of $^{125}$I-CCK-8 binding) and 50 µl of 500 pM $^{125}$I-CCK-8 (i.e. final concentration of 50 pM) were added to 400 µl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results

Effects of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 µM CCK) binding.

Drug displacement studies were performed with at least 10 concentrations of compounds of Formula I and the IC$_{50}$ values were determined by regression analysis IC$_{50}$ refers to the concentration of the compound required to inhibit 50% of specific binding of 125I-CCK-8.

The data in Table I were obtained for compounds of Formula I.

TABLE I

CCK RECEPTOR BINDING RESULTS
IC$_{50}$ (nM)

| Compound of Ex # | $^{125}$I-CCK Pancreas | $^{125}$I-CCK Brain |
|---|---|---|
| 1 | 17 | 5.7 |
| 2 | 612 | 137 |
| 3 | 505 | 78 |
| 4 | 4125 | 106 |
| 5 | 4320 | 71.8 |
| 6 | >3000 | 160 |
| 7 | >3000 | 130 |
| 8 | 3200 | 9.8 |
| 9 | >3000 | 880 |
| 10 | 900 | 94 |
| 11 | 2300 | 200 |
| 12 | >3000 | 31 |
| 13 | >3000 | 200 |
| 14 | >3000 | 1300 |
| 15 | >3000 | 3200 |
| 16 | >3000 | 390 |
| 17 | 2800 | 100 |
| 18 | >3000 | 1500 |
| 19 | 25 | 5.4 |
| 20 | 10 | 1.2 |
| 21 | 2400 | 4.9 |
| 22 | 1800 | 4.0 |
| 23 | 2400 | 3.1 |
| 24 | >3000 | 7.6 |
| 25 | 1900 | 270 |
| 26 | 4720 | 2.6 |
| 27 | 3080 | 357 |
| 28 | >3000 | 1.35 |
| 29 | 7.9 | 144 |
| 30 | 2700 | 42 |
| 31 | 3450 | 443 |
| 32 | 3800 | 11.8 |
| 33 | >3000 | 2.74 |
| 34 | >3000 | 0.58 |
| 35 | 5310 | 18.3 |
| 36 | >3000 | 600 |
| 37 | 3730 | 14.8 |
| 38 | 1600 | 23.5 |
| 39 | >3000 | 56.2 |
| 40 | >3000 | 52 |
| 41 | >3000 | 2.52 |
| 42 | 711 | 23.5 |
| 43 | 18.4 | 0.88 |
| 44 | 120 | 2.44 |
| 45 | 956 | 303 |
| 46 | 28.2 | 0.44 |
| 47 | 23.4 | 0.089 |
| 48 | 31.4 | 2.14 |
| 49 | 57.2 | 6.5 |
| 50 | 815 | 75 |
| 51 | 1920 | 0.305 |
| 52 | 11.7 | 2.4 |
| 53 | >3000 | 586 |
| 54 | 399 | 3.18 |
| 55 | 337 | 2.47 |
| 56 | >3000 | 6.75 |
| 57 | 16.7 | 3.24 |
| 58 | 2434 | 0.143 |
| 59 | 8.92 | 5.55 |
| 60 | 7.16 | 2.17 |
| 61 | 36.1 | 0.594 |

TABLE I-continued

CCK RECEPTOR BINDING RESULTS
IC$_{50}$ (nM)

| Compound of Ex # | $^{125}$I-CCK Pancreas | $^{125}$I-CCK Brain |
|---|---|---|
| 62 | 21.4 | 0.938 |
| 63 | 4.39 | 0.346 |
| 64 | 3.59 | 0.38 |
| 65 | 17.2 | 2.75 |
| 66 | 14.2 | 6.05 |
| 67 | 310 | 0.47 |
| 68 | 3.48 | 34.3 |
| 69 | 515 | 0.06 |
| 70 | 10.5 | 44.6 |

We claim:

1. A compound of formula (I), or a pharmaceutically acceptable salt thereof:

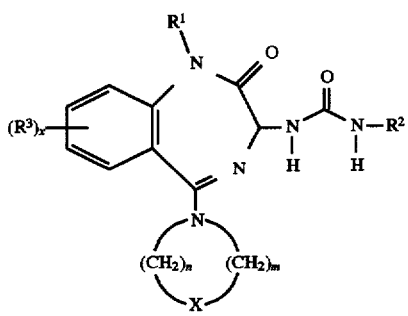

wherein:

X represents O, S, NR$^4$ or CH$_2$ where R$^4$ represents H, C$_{1-4}$alkyl, CO$_2$R$^a$, COR$^a$ or SO$_2$R$^a$ where R$^a$ is C$_{1-6}$alkyl, optionally substituted phenyl or benzyl optionally substituted in the phenyl ring by one or more substituents, where the phenyl substituents are selected from C$_{1-4}$alkyl, C$_{1-4}$alkoxy, halo and trifluoromethyl;

R$^1$ represents H, C$_{1-6}$ alkyl, C$_{3-7}$ cycloalkyl, cyclopropylmethyl, (CH$_2$),imidazolyl, (CH$_2$)$_r$ tetrazolyl, (CH$_2$)$_r$triazolyl, where r is 1, 2 or 3, CH$_2$CO$_2$R$^5$, where R$^5$ is C$_{1-4}$alkyl or a group CH$_2$CONR$^6$R$^7$ where R$^6$ and R$^7$ each independently represents H or C$_{1-4}$ alkyl, or R$^6$ and R$^7$ together form a chain (CH$_2$)$_p$ where p is 4 or 5;

R$^2$ represents a phenyl group optionally substituted by one or more substituents selected from C$_{1-6}$ alkyl, halo, hydroxy, OR$^5$ where R$^5$ is as previously defined, (CH$_2$)$_q$ tetrazolyl, optionally substituted in the tetrazole ring by C$_{1-4}$alkyl, (CH$_2$)$_q$ imidazolyl, (CH$_2$)$_q$ triazolyl where q is 0, 1, 2 or 3, 5-hydroxy-4-pyrone, NR$^6$R$^7$, NR$^9$COR$^5$, NR$^9$CONR$^{9a}$R$^5$ where R$^9$ and R$^{9a}$ are each independently H or C$_{1-4}$alkyl and R$^5$ is as previously defined, CONR$^6$R$^7$ where R$^6$ and R$^7$ are as previously defined, SO(C$_{1-6}$alkyl), SO$_2$(C$_{1-6}$alkyl), trifluoromethyl, CONHSO$_2$R$^8$, SO$_2$NHCOR$^8$ where R$^8$ is C$_{1-6}$alkyl, optionally substituted aryl, 2,2-difluorocyclopropane or trifluoromethyl, SONHR$^{10}$, where R$^{10}$ is a nitrogen containing heterocycle selected from the group consisting of thiazole, thiadiazole and pyrazine; B(OH)$_2$ or (CH$_2$)$_q$CO$_2$H, where q is as previously defined;

R$^2$ represents a group

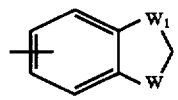

where W represents CH$_2$ or NR$^9$, where R$^9$ is as previously defined, and W$_1$ represents CH$_2$ or W and W$_1$ each represent O;

R$^3$ represents C$_{1-6}$ alkyl, halo, or NR$^6$R$^7$, where R$^6$ and R$^7$ are as previously defined;

m is 2, 3 or 4;

n is 1, 2, 3, 4, 5, 6, 7 or 8 when X is CH$_2$, or 2, 3, 4, 5, 6, 7 or 8 when X is O, S or NR$^4$;

x is 0, 1,2 or 3.

2. A compound as claimed in claim 1 wherein

R$^1$ represents C$_{1-6}$alkyl, C$_{3-7}$cycloalkyl, cyclopropylmethyl, CH$_2$CO$_2$R$^5$ (where R$^5$ is C$_{1-4}$alkyl) or a group CH$_2$CONR$^6$R$^7$ (where R$^6$ and R$^7$ each independently represents H or C$_{1-4}$alkyl, or R$^6$ and R$^7$ together form a chain (CH$_2$)$_p$ where p is 4 or 5); and R$^2$ represents a phenyl group optionally substituted by one or more substituents selected from C$_{1-6}$alkyl, halo, hydroxy, OR$^5$ (where R$^5$ is as previously defined), (CH$_2$)$_q$-tetrazolyl optionally substituted in the tetrazole ring by C$_{1-4}$alkyl (CH$_2$)$_q$-imidazolyl (CH$_2$)$_q$-triazolyl (where q is 1, 2 or 3), 5-hydroxy-4-pyrone, NR$^6$R$^7$, NR$^9$COR$^5$, NR$^9$COR$^{9a}$R$^5$ (where R$^9$ and R$^{9a}$ are each independently H or C$_{1-4}$alkyl) CONR$^6$R$^7$ (where R$^6$ and R$^7$ are as previously defined), SO(C$_{1-6}$alkyl), SO$_2$ (C$_{1-6}$alkyl), trifluoromethyl, CONHSO$_2$R$^8$, SO$_2$NHCOR$^8$ (where R$^8$ is C$_{1-6}$alkyl, optionally substituted aryl, 2,2-difluorocyclopropane or trifluoromethyl), SO$_2$NHR$^{10}$ (where R$^{10}$ is a nitrogen containing heterocycle), B(OH)$_2$, (CH$_2$)$_s$CO$_2$H, where s is zero, 1 or 2; or R$^2$ represents a group

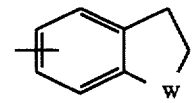

where W represents CH$_2$ or NR$^9$, and R$^9$ is as previously defined, and m is 2.

3. A compound as claimed in claim 1 represented by formula (Ia):

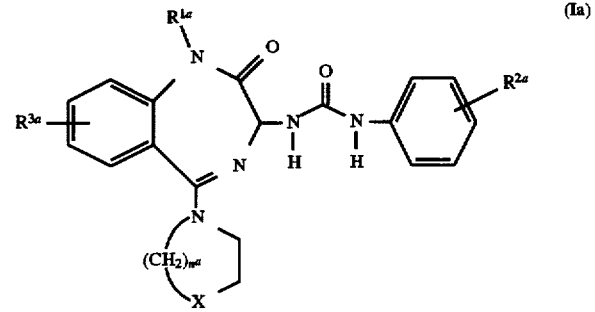

wherein:

X is as defined for formula (I);

R$^{1a}$ represents C$_{1-6}$alkyl, C$_{3-7}$cycloalkyl, cyclopropylmethyl, CH$_2$CO$_2$R$^5$ (where R$^5$ is C$_{1-4}$alkyl)

or a group $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);

$R^{2a}$ represents H, $C_{1-6}$alkyl, halo, hydroxy, $OR^5$ (where $R^5$ is as previously defined), $(CH_2)_q$-tetrazole optionally substituted on N by $C_{1-4}$alkyl, $(CH_2)_q$-imidazolyl, $CONR^6R^7$ (where $R^6$ and $R^7$ are as previously defined), trifluoromethyl, $CONHSO_2R^8$, $SO_2NHCOR^8$ (where $R^8$ is $C_{1-4}$alkyl, optionally substituted aryl or trifluoromethyl), $SO_2NHR_{10}$ (where $R_{10}$ is a nitrogen containing heterocycle), cyclopropyl or a group $(CH_2)_qCO_2H$, where q is zero, 1 or 2;

$R^{3a}$ represents H, $C_{1-6}$alkyl or halo;

$n^a$ is 1, 2 or 3 when X is $CH_2$, or 2 or 3 when X is O, S or $NR^4$.

4. A compound as claimed in claim 3 wherein $R^{2a}$ represents H, $C_{1-6}$alkyl, halo, $(CH_2)_q$-tetrazolyl, $(CH_2)_q$-imidazolyl, $CONHSO_2R^8$, $SO_2NHCOR^8$ (where $R^8$ is $C_{1-4}$alkyl, optionally substituted aryl or trifluoromethyl) or $(CH_2)_qCO_2H$, where q is zero, 1 or 2.

5. A compound as claimed in claim 1 wherein X represents O, S, $NR^{4b}$ or $CH_2$, where $R^{4b}$ represents H or $C_{1-4}$alkyl;

$R^1$ represents $C_{1-6}$alkyl;

$R^2$ represents a phenyl group optionally substituted by one or two substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, where q is 0, 1, 2 or 3, 5-hydroxy-4-pyrone, $NR^6R^7$ (where $R^6$ and $R^7$ are as previously defined), $NR^9COR^5$, $NR^9CONR^9R^5$ where $R^5$, $R^9$ and $R^{9a}$ are as previously defined, $CONR^6R^7$ or trifluoromethyl; or $R^2$ represents a group

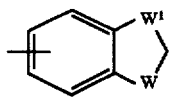

where W and $W^1$ are as previously defined;

m is 2;

n is 1, 2, 3, 4 or 5 when X is $CH_2$, or 2, 3, 4 or 5 when X is O, S or $NR^{4b}$; and x is 0.

6. A compound as claimed in claim 1 wherein $R^2$ is phenyl substituted in the 3-position by methyl or ethyl.

7. A compound as claimed in claim 1 wherein $R^2$ is phenyl substituted in the 3-position by 5-hydroxy-4-pyrone, or $R^2$ is

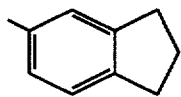

8. A compound as claimed in claim 1 wherein the substituent

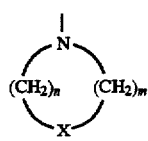

represents homopiperidine, N-methylpiperazine, heptamethyleneimine or octamethyleneimine.

9. A compound as claimed in claim 1 selected from:

N-[3(R,S)-2,3-dihydro-1-methyl-2-oxo-5-(piperidin-1-yl)-1H-1,4-benzodiazepin-3-yl]N'-[3-methylphenyl]urea;

N-[3(R,S)-2,3-dihydro-1-methyl-2-oxo-5-(pyrrolidin-1-yl)-1H-1,4-benzodiazepin-3-yl]N'-[3-methylphenyl]urea;

N-[3(R,S)-2,3-dihydro-1-methyl-5-(morpholin-4-yl)-2-oxo-1H-1,4-benzodiazepin-3-yl]N'-[3-methylphenyl]urea;

N-[3(R,S)-2,3-dihydro-1-methyl-5-(4-methylpiperazin-1-yl)-2-oxo-1H-1,4-benzodiazepin-3-yl]N'-[3-methylphenyl]urea;

N-[3(R,S)-2,3-dihydro-1-methyl-5-(4-methylpiperazin-1-yl)-2-oxo-1H-1,4-benzodiazepin-3-yl]N'-[3-ethylphenyl]urea;

N-[3(R,S)-2,3-dihydro-1-methyl-5-(4-methylpiperazin-1-yl)-2-oxo-1H-1,4-benzodiazepin-3-yl]N'-[4-chlorophenyl]urea;

N-[3(R,S)-2,3-dihydro-1-methyl-5-(4-methylpiperazin-1-yl)-2-oxo-1H-1,4-benzodiazepin-3-yl]N'-[4-methylphenyl]urea;

N-[3(R,S)-2,3-dihydro-5-(4-methylpiperazin-1-yl)-2-oxo-1-propyl-1H-1,4-benzodiazepin-3-yl]N'-[3-methylphenyl]urea;

N-[3(R,S)-2,3-dihydro-1-methyl-5-(4-piperazin-1-yl)-2-oxo-1H-1,4-benzodiazepin-3-yl]N'-[3-methylphenyl]urea;

N-[3(R,S)-2,3-dihydro-1-methyl-5-(4-methylpiperazin-1-yl)-2-oxo-1H-1,4-benzodiazepin-3-yl]N'-[3-methoxyphenyl]urea;

N-[3(R,S)-2,3-dihydro-1-methyl-5-(4-methylpiperazin-1-yl)-2-oxo-1H-1,4-benzodiazepin-3-yl]N'-[3-hydroxyphenyl]urea;

N-[3(R,S)-2,3-dihydro-5-(4-methylpiperazin-1-yl)-2-oxo-1-propyl-1H-1,4-benzodiazepin-3-yl]N'-[3-methoxyphenyl]urea;

N-[3(R,S)-2,3-dihydro-1-methyl-2-oxo-5-(4-methylpiperazin-1-yl)-1H-1,4-benzodiazepin-3-yl]N'-[3-(2-methyltetrazol-5-yl)phenyl]urea;

N-[3(R,S)-2,3-dihydro-1-methyl-2-oxo-5-(4-methylpiperazin-1-yl)-1H-1,4-benzodiazepin-3-yl]N'-[3-(1-methyltetrazol-5-yl)phenyl]urea;

N-[3(R,S)-2,3-dihydro-1-methyl-2-oxo-5-(4-methylpiperazin-1-yl)-1H-1,4-benzodiazepin-3-yl]N'-[3-(N,N-dimethylcarboxamido)phenyl]urea;

N-[3(R,S)-2,3-dihydro-5-(4-homopiperazin-1-yl)-1-methyl-2-oxo-1H-1,4-benzodiazepin-3-yl]N'-[3-methylphenyl]urea;

N-[3(R,S)-2,3-dihydro-1-methyl-5-(4-methylhomopiperazin-1-yl)-2-oxo-1H-1,4-benzodiazepin-3-yl]N'-[3-methylphenyl]urea;

N-[3(R,S)-2,3-dihydro-1-methyl-2-oxo-5-(4-methylpiperazin-1-yl)-1H-1,4-benzodiazepin-3-yl]N'-[3-(N-ethylcarboxamido)phenyl]urea;

N-[3(R,S)-2,3-dihydro-1-methyl-2-oxo-5-(piperidin-1-yl)-1H-1,4-benzodiazepin-3-yl]N'-[3-ethylphenyl]urea;

N-[3(R,S)-2,3-dihydro-5-(homopiperidin-1-yl)-1-methyl-2-oxo-1H-1,4-benzodiazepin-3-yl]N'-[3-methylphenyl]urea;

N-[3(R,S)-2,3-dihydro-5-(4-methylpiperazin-1-yl)-2-oxo-1-propyl-1H-1,4-benzodiazepin-3-yl]N'-[3-ethylphenyl]urea;

N-[3(R,S)-2,3-dihydro-5-(4-methylpiperazin-1-yl)-1-(2-methylpropyl)-2-oxo-1H-1,4-benzodiazepin-3-yl]N'-[3-methylphenyl]urea;

N-[3(R,S)-2,3-dihydro-5-(4-methylpiperazin-1-yl)-1-(2-methylpropyl)-2-oxo-1 H-1,4-benzodiazepin-3-yl]N'-[3-ethylphenyl]urea;

(−)-N-[2,3-dihydro-5-(4-methylpiperazin-1-yl)-2-oxo-1-propyl-1H-1,4-benzodiazepin-3-yl]N'-[3-methylphenyl]urea;

(+)-N-[2,3-dihydro-5-(4-methylpiperazin-1-yl)-2-oxo-1-propyl-1H-1,4-benzodiazepin-3-yl]N'-[3-methylphenyl]urea;

(−)-N-[2,3-dihydro-5-(4-methylpiperazin-1-yl)-1-(2-methylpropyl)-2-oxo-1H-1,4-benzodiazepin-3-yl]-N'-[3-ethylphenyl]urea;

(+)-N-[2,3-dihydro-5-(4-methylpiperazin-1-yl)-1-(2-methylpropyl)-2-oxo-1H-1,4-benzodiazepin-3-yl]-N'-[3-ethylphenyl]urea;

(−)-N-[2,3-dihydro-5-(homopiperidin-1-yl)-1-methyl-2-oxo-1H-1,4-benzodiazepin-3-yl]-N'-[3-methylphenyl]urea;

(+)-N-[2,3-dihydro-5-(homopiperidin-1-yl)-1-methyl-2-oxo-1H-1,4-benzodiazepin-3-yl]-N'-[3-methylphenyl]urea;

N-[3(R,S)-2,3-dihydro-1-methyl-2-oxo-5-(4-methylpiperazin-1-yl)-1H-1,4-benzodiazepin-3-yl]-N'-[3-trifluoromethylphenyl]urea;

N-[3(R,S)-2,3-dihydro-1-methyl-2-oxo-5-(4-methylpiperazin-1-yl)-1H-1,4-benzodiazepin-3-yl]-N'-phenylurea;

N-[3(R,S)-2,3-dihydro-5-(4-methylpiperazin-1-yl)-2-oxo-1-propyl-1H-1,4-benzodiazepin-3-yl]-N'-[3-trifluoromethylphenyl]urea;

N-[3(R,S)-2,3-dihydro-5-(4-methylpiperazin-1-yl)-2-oxo-1-propyl-1H-1,4-benzodiazepin-3-yl]-N'-[5-indanyl]urea;

(−)-N-[2,3-dihydro-5-(4-methylpiperazin-1-yl)-2-oxo-1-propyl-1H-1,4-benzodiazepin-3-yl]-N'-[5-indanyl]urea;

N-[3(R,S)-2,3-dihydro-5-(4-methylpiperazin-1-yl)-2-oxo-1-propyl-1H-1,4-benzodiazepin-3-yl]-N'-[3-propylphenyl]urea;

N-[3(R,S)-2,3-dihydro-2-oxo-5-(piperazin-1-yl)-1-propyl-1H-1,4-benzodiazepin-3-yl]-N'-[3-methylphenyl]urea;

N-[3(R,S)-2,3-dihydro-5-(4-ethylpiperazin-1-yl)-2-oxo-1-propyl-1H-1,4-benzodiazepin-3-yl]-N'-[3-methylphenyl]urea;

N-[3(R,S)-2,3-dihydro-7-methyl-5-(4-methylpiperazin-1-yl)-2-oxo-1-propyl-1H-1,4-benzodiazepin-3-yl]-N'-[3-methylphenyl]urea;

N-[3(R,S)-2,3-dihydro-5-(4-methylpiperazin-1-yl)-2-oxo-1-propyl-1H-1,4-benzodiazepin-3-yl]-N'-[3-(acetylamino)phenyl]urea;

(+)-N-[2,3-dihydro-5-(4-methylpiperazin-1-yl)-2-oxo-1-propyl-1H-1,4-benzodiazepin-3-yl]-N'-[3-methylaminocarbonylamino)phenyl]urea;

(−)-N-[2,3-dihydro-5-(4-methylpiperazin-1-yl)-2-oxo-1-propyl-1H-1,4-benzodiazepin-3-yl]-N'-[3-(dimethylamino) phenyl]urea;

N-[3(R,S)-2,3-dihydro-8-methyl-5-(4-methylpiperazin-1-yl)-2-oxo-1-propyl-1H-1,4-benzodiazepin-3-yl]-N'-[3-methylphenyl]urea;

N-[3(R,S)-2,3-dihydro-5-(heptamethyleneimin-1-yl)-1-methyl-2-oxo-1H-1,4-benzodiazepin-3-yl]-N'-[3-methylphenyl]urea;

N-[3(R,S)-2,3-dihydro-2-oxo-5-(piperidin-1-yl)-1-propyl-1H-1,4-benzodiazepin-3-yl]-N'-[3-methylphenyl]urea;

N-[3(R,S)-2,3-dihydro-8-dimethylamino-5-(4-methylpiperazin-1-yl)-2-oxo-1-propyl-1H-1,4-benzodiazepin-3-yl]-N'-[3-methylphenyl]urea;

N-[3(R,S)-2,3-dihydro-5-(homopiperidin-1-yl)-1-methyl-2-oxo-1H-1,4-benzodiazepin-3-yl]-N'-[5-indanyl]urea;

N-[3(R,S)-2,3-dihydro-5-(homopiperidin-1-yl)-2-oxo-1-propyl-1H-1,4-benzodiazepin-3-yl]-N'-[3-methylphenyl]urea;

N-[3(R,S)-2,3-dihydro-5-(homopiperidin-1-yl)-1-methyl-2-oxo-1H-1,4-benzodiazepin-3-yl]-N'-[3-trifluoromethylphenyl]urea;

N-[3(R,S)-2,3-dihydro-5-(homopiperidin-1-yl)-1-methyl-2-oxo-1H-1,4-benzodiazepin-3-yl]-N'-[3-(dimethylamino)phenyl]urea;

N-[3(R,S)-2,3-dihydro-5-(homopiperidin-1-yl)-1-methyl-2-oxo-1H-1,4-benzodiazepin-3-yl]-N'-[4-t-butylphenyl]urea;

(−)-N-[2,3-dihydro-5-(heptamethyleneimin-1-yl)-1-methyl-2-oxo-1H-1,4-benzodiazepin-3-yl]-N'-[3-methylphenyl]urea;

(+)-N-[2,3-dihydro-5-(heptamethyleneimin-1-yl)-1-methyl-2-oxo-1H-1,4-benzodiazepin-3-yl]-N'-[3-methylphenyl]urea;

N-[3(R,S)-2,3-dihydro-5-(4-methylpiperazin-1-yl)-2-oxo-1-propyl-1H-1,4-benzodiazepin-3-yl]-N'-[4-(dimethylamino)phenyl]urea;

N-[3(R,S)-2,3-dihydro-5-(homopiperidin-1-yl)-1-methyl-2-oxo-1H-1,4-benzodiazepin-3-yl]-N'-[4-isopropylphenyl]urea;

N-[3(R,S)-2,3-dihydro-2-oxo-1-propyl-5-(thiomorpholin-4-yl)-1H-1,4-benzodiazepin-3-yl]-N'-[3-methylphenyl]urea;

N-[3(R,S)-2,3-dihydro-5-(4-methylpiperazin-1-yl)-2-oxo-1-propyl-1H-1,4-benzodiazepin-3-yl]-N'-[1-methyl-6-indolinyl]urea;

N-[3(R,S)-2,3-dihydro-5-(homopiperidin-1-yl)-1-methyl-2-oxo-1H-1,4-benzodiazepin-3-yl]-N'-[3,4-difluorophenyl]urea;

(−)-N-[2,3-dihydro-5-(homopiperidin-1-yl)-1-methyl-2-oxo-1H-1,4-benzodiazepin-3-yl]-N'-[5-indanyl]urea;

(+)-N-[2,3-dihydro-5-(homopiperidin-1-yl)-1-methyl-2-oxo-1H-1,4-benzodiazepin-3-yl]-N'-[5-indanyl]urea;

N-[3(R,S)-2,3-dihydro-5-(homopiperidin-1-yl)-1-methyl-2-oxo-1H-1,4-benzodiazepin-3-yl]-N'-[3-fluorophenyl]urea;

N-[3(R,S)-2,3-dihydro-1-methyl-5-(octamethyleneimin-1-yl)-2-oxo-1H-1,4-benzodiazepin-3-yl]-N'-[3-methylphenyl]urea;

N-[3(R,S)-2,3-dihydro-5-(homopiperidin-1-yl)-1-methyl-2-oxo-1H-1,4-benzodiazepin-3-yl]-N'-[3-(5-hydroxy-4-pyron-2-yl)phenyl]urea;

N-[3(R,S)-2,3-dihydro-5-(homopiperidin-1-yl)-1-methyl-2-oxo-1H-1,4-benzodiazepin-3-yl]-N'-[3-ethylphenyl]urea;

N-[3(R,S)-2,3-dihydro-1-ethyl-5-(homopiperidin-1-yl)-2-oxo-1H-1,4-benzodiazepin-3-yl]-N'-[3-methylphenyl]urea;

N-[3(R,S)-2,3-dihydro-1-methyl-2-oxo-5-(thiomorpholin-4-yl)-1H-1,4-benzodiazepin-3-yl]-N'-[3-methylphenyl]urea;

N-[3(R,S)-2,3-dihydro-5-(homopiperidin-1-yl)-1-methyl-2-oxo-1H-1,4-benzodiazepin-3-yl]-N'-phenyl urea;

(−)-N-[2,3-dihydro-5-(homopiperidin-1-yl)-1-methyl-2-oxo-1H-1,4-benzodiazepin-3-yl]-N'-[3-ethylphenyl]urea;

(+)-N-[2,3-dihydro-5-(homopiperidin-1-yl)-1-methyl-2-oxo-1H-1,4-benzodiazepin-3-yl ]-N'-[3-ethylphenyl]urea;

(−)-N-[2,3-dihydro-2-oxo-1-propyl-5-(thiomorpholin-4-yl)-1H-1,4-benzodiazepin-3-yl]-N'-[3-methylphenyl]urea;

(+)-N-[2,3-dihydro-2-oxo-1-propyl-5-(thiomorpholin-4-yl)-1H-1,4-benzodiazepin-3-yl]-N'-[3-methylphenyl]urea;

N-[3(R,S)-2,3-dihydro-5-(homopiperidin-1-yl)-1-methyl-2-oxo-1H-1,4-benzodiazepin-3-yl]-N'-[3,4-(methylenedioxy)phenyl]urea;

N-[3(R,S)-2,3-dihydro-5-(homopiperidin-1-yl)-1-methyl-2-oxo-1H-1,4-benzodiazepin-3-yl]-N'-[3-fluoro-4-methylphenyl]urea;

and pharmaceutically acceptable salts thereof.

10. A pharmaceutical composition comprising a compound as claimed in claim 1 in association with a pharmaceutically acceptable carrier.

11. A method for the treatment of gastric ulcer, which method comprises administration to a patient in need thereof a CCK and/or gastrin reducing amount of a compound according to claim 1.

* * * * *